US011439650B2

(12) United States Patent
Brough et al.

(10) Patent No.: US 11,439,650 B2
(45) Date of Patent: *Sep. 13, 2022

(54) THERMO-KINETIC MIXING FOR PHARMACEUTICAL APPLICATIONS

(71) Applicants: BOARD OF REGENTS, THE UNIVERSITY OF TEXAS SYSTEM, Austin, TX (US); DISPERSOL TECHNOLOGIES, LLC, Georgetown, TX (US)

(72) Inventors: Chris Brough, Austin, TX (US); James W. McGinity, Austin, TX (US); Dave A. Miller, Round Rock, TX (US); James C. DiNunzio, Bridgewater, NJ (US); Robert O. Williams, III, Austin, TX (US)

(73) Assignees: BOARD OF REGENTS, THE UNIVERSITY OF TEXAS SYSTEM, Austin, TX (US); DISPERSOL TECHNOLOGIES, LLC, Georgetown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/866,676

(22) Filed: May 5, 2020

(65) Prior Publication Data

US 2020/0261473 A1    Aug. 20, 2020

Related U.S. Application Data

(60) Continuation of application No. 16/012,025, filed on Jun. 19, 2018, now Pat. No. 10,668,085, which is a continuation of application No. 15/154,083, filed on May 13, 2016, now Pat. No. 10,022,385, which is a continuation of application No. 13/942,199, filed on Jul. 15, 2013, now Pat. No. 9,339,440, which is a division of application No. 12/196,154, filed on Aug. 21, 2008, now Pat. No. 8,486,423.

(60) Provisional application No. 61/050,922, filed on May 6, 2008, provisional application No. 60/957,044, filed on Aug. 21, 2007.

(51) Int. Cl.
| | |
|---|---|
| *A61J 3/00* | (2006.01) |
| *A61K 47/32* | (2006.01) |
| *A61K 47/38* | (2006.01) |
| *A61K 31/573* | (2006.01) |
| *A61K 9/14* | (2006.01) |
| *A61K 9/16* | (2006.01) |
| *A61K 9/20* | (2006.01) |
| *A61J 3/07* | (2006.01) |
| *A61J 3/10* | (2006.01) |
| *A61K 31/343* | (2006.01) |
| *A61K 31/496* | (2006.01) |

(52) U.S. Cl.
CPC .............. *A61K 31/573* (2013.01); *A61J 3/00* (2013.01); *A61J 3/07* (2013.01); *A61J 3/10* (2013.01); *A61K 9/146* (2013.01); *A61K 9/1694* (2013.01); *A61K 9/2077* (2013.01); *A61K 31/343* (2013.01); *A61K 31/496* (2013.01); *A61K 47/32* (2013.01); *A61K 47/38* (2013.01)

(58) Field of Classification Search
CPC ....... A61J 3/10; A61J 3/07; A61J 3/00; A61K 9/146; A61K 31/343; A61K 31/496; A61K 31/573; A61K 47/32; A61K 47/38; A61K 9/1694; A61K 9/2077
See application file for complete search history.

(56) References Cited

U.S. PATENT DOCUMENTS

| | | | |
|---|---|---|---|
| 4,152,076 A | 5/1979 | Driskill | |
| 4,230,615 A * | 10/1980 | Crocker | ............ B01F 15/00181 366/144 |
| 4,628,073 A | 12/1986 | Fisher | |
| 4,789,597 A | 12/1988 | Gupta et al. | |
| 5,456,923 A | 10/1995 | Nakamichi et al. | |
| 5,895,790 A | 4/1999 | Good | |
| 6,709,146 B1 | 3/2004 | Little et al. | |
| 8,486,423 B2 | 7/2013 | Brough et al. | |
| 9,339,440 B2 * | 5/2016 | Brough | ................ A61K 9/2077 |

(Continued)

FOREIGN PATENT DOCUMENTS

| | | |
|---|---|---|
| CN | 1747720 | 3/2006 |
| JP | H07159587 | 6/1995 |

(Continued)

OTHER PUBLICATIONS

Aitken-Nichol, et al., "Hot melt extrusion of acrylic films," *Pharmaceutical Research*, 13:804-8, 1996.

(Continued)

*Primary Examiner* — Michael B. Pallay
(74) *Attorney, Agent, or Firm* — Parker Highlander PLLC

(57) ABSTRACT

Compositions and methods for making a pharmaceutical dosage form include making a pharmaceutical composition that includes one or more active pharmaceutical ingredients (API) with one or more pharmaceutically acceptable excipients by thermokinetic compounding into a composite. Compositions and methods of preprocessing a composite comprising one or more APIs with one or more excipients include thermokinetic compounding, comprising thermokinetic processing the APIs with the excipients into a composite, wherein the composite can be further processed by conventional methods known in the art, such as hot melt extrusion, melt granulation, compression molding, tablet compression, capsule filling, film-coating, or injection molding.

10 Claims, 13 Drawing Sheets

(56) References Cited

U.S. PATENT DOCUMENTS

| | | | |
|---|---|---|---|
| 9,545,361 | B1 | 1/2017 | Brough |
| 10,022,385 | B2 | 7/2018 | Brough et al. |
| 10,668,085 | B2* | 6/2020 | Brough .................... A61J 3/07 |
| 2001/0007678 | A1* | 7/2001 | Baert .................. A61K 9/1652 |
| | | | 424/464 |
| 2002/0010168 | A1 | 1/2002 | Ammon et al. |
| 2005/0158376 | A1 | 7/2005 | Sardi et al. |
| 2006/0204572 | A1 | 9/2006 | Higuchi et al. |
| 2006/0264497 | A1 | 11/2006 | Zeligs |
| 2017/0333404 | A1 | 11/2017 | Miller et al. |

FOREIGN PATENT DOCUMENTS

| | | |
|---|---|---|
| JP | 2004-043485 | 2/2004 |
| JP | 2005-501820 | 1/2005 |
| JP | 2005-263758 | 9/2005 |
| JP | 2007-161588 | 6/2007 |
| WO | WO 2003/000238 | 1/2003 |
| WO | WO 2004/010976 | 2/2004 |
| WO | WO 2004/069138 | 8/2004 |
| WO | WO 2005/018611 | 3/2005 |
| WO | WO 2005/046696 | 5/2005 |
| WO | WO 2006/049433 | 5/2006 |
| WO | WO 2009/026461 | 2/2009 |
| WO | WO 2012/026407 | 3/2012 |
| WO | WO 2012/116238 | 8/2012 |

OTHER PUBLICATIONS

Breitenbach, et al., "Melt extrusion can bring new benefits to HIV therapy: the example of Kaletra tablets," *American Journal of Drug Delivery*, 4:61-4, 2006.

Breitenbach, et al., "Melt extrusion: from process to drug delivery technology," *European Journal of Pharmaceutics and Biopharmaceutics*, 54:107-17, 2002.

Brittain, et al., "Effects of polymorphism and solid-state solvation on solubility and dissolution rate," *Polymorphisms in Pharmaceutical Solids, 2nd Edition: Chapter 12*, 279-330, 1999.

Chen, et al., "Preparation of cyclosporine A nanoparticles by evaporative precipitation into aqueous solution," *International Journal of Pharmaceutics*, 242: 3-14, 2002.

Chiou, et al., "Preparation and dissolution characteristics of several fast-release solid dispersions of griseofulvin," *Journal of Pharmaceutical Sciences*, 58:1505-10, 1969.

Chowdary, et al., "Dissolution, bioavailability and ulcerogenic studies on solid dispersions of indomethacin in water soluble cellulose polymers," *Drug Development and Industrial Pharmacy*, 20:799-813, 1994.

Concise Encyclopedia of Plastics, pp. 287, 2000.

Conesa, et al. "Thermogravimetric studies on the thermal decomposition of polyethylene," *J. of Analytical and Applied Pyrolysis*, 36:1-15, 1996.

Crowley, et al., "The influence of guaifenesin and ketoprofen on the properties of hot-melt extruded polyethlylene oxide films," *European Journal of Pharmaceutical Sciences*, 22:409-18, 2004.

De Brabander, et al., "Development and evaluation of sustained release mini-matrices prepared via hot melt extrusion," *Journal of Controlled Release*, 89:235-47, 2003.

Derle, Essential of Physical Pharmacy, pp. 167, 2008.

DiNunzio, et all, "Fusion processing of itraconazole solid dispersions by kinetisol dispersing: a comparative study to hot melt extrusion," *J. Pharm. Sci.*, 99:1239-53, 2010.

Dittgen, et al., "Hot spin mixing—a new technology to manufacture solid dispersions—Part 1: Testosterone," *Pharmazie*, 50:225-6, 1995.

Dunaway, 1st Edition: Physical Chemistry, pp. 72-73, 2012.

Edited by Pharmaceutical and Medical Device Regulatory Science Society of Japan, Cosmetic Material Standard, 2nd version codex I, pp. 406-409, 1984 (partial translation).

Encyclopedia Dictionary of Chemistry 3, cutdown version, section of "hydrogenated oil", 22th edition, pp. 500-501, 1978 (partial translation).

Extended European Search Report, Application No. 08798412.6, dated Jan. 23, 2013.

Forster, et al., "Selection of excipients for melt extrusion with two poorly water-soluble drugs by solubility parameter calculation and thermal analysis," *International Journal of Pharmaceutics*, 226:147-61, 2001.

Gaisford, et al., Pharmaceutical Isothermal Calorimetry, pp. 185, 2007.

Ghosh, et al., Theroy and Practice of Contemporary Pharmaceutics, pp. 218, 2004.

Glomme, et al., "Comparison of a miniaturized shake-flask solubility method with automated potentiometric acid/base titrations and calculated solubilities," *Journal of Pharmaceutical Sciences*, 94:1-16, 2005.

Goldberg, et al., "Increasing dissolution rates and gastrointertinal absorption of drugs via solid solutions and eutectic mixtures II," *Journal of Pharmaceutical Sciences*, 55:482-7, 1966.

Goldberg, et al., "Increasing dissolution rates and gastrointertinal absorption of drugs via solid solutions and eutectic mixtures I," *Journal of Pharmaceutical Sciences*, 54:1145-8, 1965.

Goldberg, et al., "Increasing dissolution rates and gastrointertinal absorption of drugs via solid solutions and eutectic mixtures IV," *Journal of Pharmaceutical Sciences*, 55:581-3, 1966.

Gopakumar, et al., "Compounding of nanocomposites by thermokinetic mixing," *Journal of Applied Polymer Science*, 96:1557-63, 2005.

Gopakumar, et al., "Polypropylene/graphite nanocomposites by thermo-kinetic mixing" *Polymer Engineering and Science*, 44:1162-9, 2004.

Hamaura, et al., Interaction between water and poly(vinylpyrrolidone) containing polyethylene glycol, *Pharmaceutical Sciences*, 88:1228-1233, 1999.

Harper, et al., Plastic Materials and Processes: A Concise Encyclopedia, pp. 215, 2003.

Hirayama, et al., "Effect of 2-hydroxypropyl-β-cyclodextrin on crystallization and polymorphic transition of nifedipine in solid state," *Pharma. Res.*, 11:1766-70, 1994.

Hu, et al., "Nanoparticle engineering processes for enhancing the dissolution rates of poorly water soluble drugs," *Drug Development and Industrial Pharmacy*, 30:233-45, 2004.

Hulsmann, et al., "Melt extrusion—an alternative method for enhancing the dissolution rate of 17 β-estradiol hemihydrate," *European Journal of Pharmceutics and Biopharmaceutics*, 49:237-42, 2000.

Huynh-Ba, Handbook of Stability Testing in Pharmaceutical Development, pp. 10, 2009.

ICH Harmonised Tripartite Guideline, "Impurities in new drug products Q3B(R2)," Current Step 4 version, Jun. 2, 2006.

International Search Report and Written Opinion issued in PCT/US2008/073913, dated Mar. 17, 2009.

International Search Report and Written Opinion issued in PCT/US2012/026407, dated Jun. 4, 2012.

Jung, et al., "Enhanced solubility and dissolution rate of itraconazole by a solid dispersion technique," *International Journal of Pharmaceutics*, 187:209-18, 1999.

Kolter, et al., "Hot-melt extrusion with BASF pharma polymers extrusion compendium," *BASF The Chemical Company*, 2010.

Leuner, et al., "Improving drug solubility for oral delivery using solid dispersions," *European Journal of Pharmaceutics and Biopharmaceutics*, 50:47-60, 2000.

Lipinski, "Avoiding investment in doomed drugs, is poor solubility an industry wide problem?" *Current Drug Discovery*, pp. 17-19, 2001.

Lipinski, "Drug-like properties and the causes of poor solubility and poor permeability," *Journal of Pharmacological and Toxicological Methods*, 44:235-49, 2000.

Lipinski, "Poor aqueous solubility—an industry wide problem in drug delivery," *American Pharmaceutical Review*, 5:82-5, 2002.

Lipinski, et al., "Experimental and computational approaches to estimate solubility and permeability in drug discovery and development settings," *Advanced Drug Delivery Reviews*, 23:3-25, 1997.

(56) References Cited

OTHER PUBLICATIONS

Marongiu, et al., "Thermal degradation of poly (vinyl chloride)," *J. of Analytical and Applied Pyrolsis*, 70:519-553, 2003.

McCaffrey, et al., "Thermolysis of polyethylene," *Polymer Degradation and Stability*, 47:133-9, 1995.

McGinity, et al., "Hot-melt extruded films for transmucosal and transdermal drug delivery applications," *Drug Delivery Technology*, 4:40-7, 2004.

McGinity, et al., "Hot-melt extrusion technology," *Encyclopedia of Pharmaceutical Technology*, pp. 2004-2020, 2007.

Noyes, et al., "The rate of solution of solid substances in their own solutions," *J. Amer. Chem.*, pp. 930-934, 1987.

Office Action issued in Canadian Application No. 2,697,099, dated Dec. 16, 2014.

Office Action issued in Canadian Application No. 2,697,099, dated Jan. 28, 2016.

Office Action issued in Chinese Application No. 200880112353.3, dated May 9, 2011.

Office Action issued in Chinese Application No. 200880112353.3, dated Oct. 17, 2011.

Office Action issued in European Application No. 08798412.6, dated Dec. 18, 2015.

Office Action issued in Japanese Application No. 2010-522038, dated Apr. 1, 2013.

Office Action issued in Japanese Application No. 2010-522038, dated Mar. 20, 2014.

Office Action issued in Japanese Application No. 2010-522038, dated Oct. 6, 2015.

Office Action issued in U.S. Appl. No. 12/196,154, dated Apr. 14, 2011.

Office Action issued in U.S. Appl. No. 12/196,154, dated Dec. 7, 2010.

Office Action issued in U.S. Appl. No. 12/196,154, dated Jan. 3, 2012.

Office Action issued in U.S. Appl. No. 12/196,154, dated Oct. 26, 2011.

Office Action issued in U.S. Appl. No. 13/942,199, dated Aug. 20, 2015.

Office Action issued in U.S. Appl. No. 13/942,199, dated Feb. 13, 2015.

Office Action issued in U.S. Appl. No. 13/942,199, dated Jul. 15, 2014.

Office Action issued in U.S. Appl. No. 13/942,199, dated Nov. 29, 2013.

Office Action issued in U.S. Appl. No. 15/154,083, dated Aug. 24, 2017.

Office Communication issued in corresponding Indian Application No. 201718039862, dated Dec. 11, 2019.

Office Communication issued in corresponding Japan Application No. 2010-522038, dated Feb. 13, 2019.

Park, et al., "a comparison of compounding processes for wood-fiber/thermoplastic composites," *Polymer Composites*, 18:425-31, 1997.

Paul, et al., "Polymer nanotechnology: nanocomposites," *Polymer*, 49:3187-3204, 2008.

Petereit, et al., "Formulation and process considerations affecting the stability of solid dosage forms formulated with methacrylate copolymers," *European Journal of Pharmaceutics and Biopharmaceutics*, 47:15-25, 1999.

Pharamceutical Sales 2006, "Drug information online, drugs.com, pharmaceutical research," www.drugs.com/top200_2006.html, Mar. 20, 20112.

Pinhero, et al., "The role of chain scission and chain branching in high density polyethylene during thermo-mechanical degradation," *Polymer Degradation and Stability*, 86:445-453, 2004.

Rambali, et al., "Itraconazole formulation studies of the melt-extrusion process with mixture design," *Drug Development and Industrial Pharmacy*, 29:641-52, 2003.

Rauch, "Thermodynamic Processes," First Edition, pp. 82, 2012.

Repka, et al., "Influence of plasticizers and dmgs on the physical-mechanical properties of hydroxypropylcellulose films prepared by hot melt extrusion," *Drug Development and Industrial Pharmacy*, 25:625-33, 1999.

Rogers, et al., "Solution-based particle formation of pharmaceutical powders by supercritical or compressed fluid Co2 and cryogenic spray-freezing technologies," *Drug Development and Industrial Pharmacy*, 27:1003-5, 2001.

Sekikawa, et al., "Dissolution behaviors and gastrointestinal absorption of phenytoin-polyvinylpyrrolidone coprecipitate," *Chem. Pharm. Bull.*, 26:3033-9, 1978.

Serajuddin, "Solid dispersion of poorly water-soluble drugs: early promises, subsequent problems and recent breakthroughs," *Journal of Pharmaceutical Sciences*, 88:1058-66, 1999.

Sinwat, et al., "Stabilizer choice for rapid dissolving high potency itraconazole particles formed by evaporative precipitation into aqueous solution," *International Journal of Pharmaceuticals*, 302:113-24, 2005.

Six, et al., "Characterization of solid dispersions of itraconazole and hydroxypropylmethylcellulose prepared by melt extrusion, part II," *Pharmaceutical Research*, 20:1047-54, 2003.

Six, et al., "Increased physical stability and improved dissolution properties of itraconazole, a class II drug, by solid dispersions that combine fast- and slow-dissolving polymers," *Journal of Pharmaceutical Sciences*, 93:124-31, 2004.

Six, et al., "Thermal properties of hot-stage extrudates of itraconazole and eudragit E100: phase separation and polymorphism," *Journal of Thermal Analysis and Calorimetry*, 68:591-601, 2002.

Summers, et al., "Preparation and properties of solid dispersion system containing citric acid and primidone," *Journal of Pharmaceutical Sciences*, 65:1613-17, 1976.

Verreck, et al., "Characterization of solid dispersions of itraconazole and hydroxypropylmethylcellulose prepared by melt extrusion—part I," *Int. J. Pharm.*, 251:165-74, 2003.

Verreck, et al., "Characterization of solid dispersions of itraconazole and hydroxypropylmethylcellulose prepared by melt extrusion—part I," *International Journal of Pharmaceutics*, 251:165-74, 2003.

Zhang, et al., "Properties of hot-melt extruded theophylline tablets containing poly(vinyl acetate)," *Drug Development and Industrial Pharmacy*, 26:931-42, 2000.

Zhang, et al., "Properties of sustained-release tablets prepared by hot-melt extrusion," *Pharmaceutical Development and Technology*, 4:241-50, 1999.

\* cited by examiner

THERMO-KINETIC MIXING FOR PHARMACEUTICAL APPLICATIONS

CROSS-REFERENCE TO RELATED APPLICATIONS

This application is a continuation of U.S. application Ser. No. 16/012,025, filed Jun. 19, 2018, now U.S. Pat. No. 10,668,085, which is a continuation of U.S. application Ser. No. 15/154,083, filed May 13, 2016, now U.S. Pat. No. 10,022,385, which is a continuation of U.S. application Ser. No. 13/942,199, filed Jul. 15, 2013, now U.S. Pat. No. 9,339,440, which is a divisional of U.S. application Ser. No. 12/196,154, filed Aug. 21, 2008, now U.S. Pat. No. 8,486,423, which claims priority to U.S. Provisional Application Ser. No. 60/957,044, filed Aug. 21, 2007, and U.S. Provisional Application Ser. No. 61/050,922, filed May 6, 2008, the entire contents of each of which are incorporated herein by reference.

STATEMENT OF FEDERALLY FUNDED RESEARCH

None

INCORPORATION-BY-REFERENCE OF MATERIALS FILED ON COMPACT DISC

None.

TECHNICAL FIELD OF THE INVENTION

The present invention relates in general to the field of pharmaceutical manufacturing, and more particularly, to thermo-kinetic mixing of active pharmaceutical ingredients (APIs) to produce novel dosage forms.

BACKGROUND OF THE INVENTION

Current high-throughput molecular screening methods used by the pharmaceutical industry have resulted in a vast increase in the proportion of newly discovered molecular entities which are poorly water-soluble (1-3). The therapeutic potential of many of these molecules is often not fully realized either because the molecule is abandoned during development due to poor pharmacokinetic profiles, or because of suboptimal product performance. Also, in recent years the pharmaceutical industry has begun to rely more heavily on formulational methods for improving drug solubility owing to practical limitations of salt formation and chemical modifications of neutral or weakly acidic/basic drugs (4). Consequently, advanced formulation technologies aimed at the enhancement of the dissolution properties of poorly water-soluble drugs are becoming increasingly more important to modern drug delivery.

U.S. Pat. No. 4,789,597 issued to Gupta is directed to the incorporation of chemically reactive agents on resin particles. Briefly, chemically reactive agents are locked to particles of suitable synthetic resins without wholly fluxing the resins. A high quality intermediate product is obtained having no premature reaction taking place, suitable for further techniques. The process includes the steps of intensively mixing and thermokinetically heating a batch of finely divided resin particles, with a chemically reactive agent, in an enclosed mixing chamber with a plurality of blades attached to arms rotating about a central axis within the chamber, and having a blade tip speed of at least about 18 meters per second, mixing the batch until the chemically reactive agent is locked to the resin particles, ensuring that temperature of the batch stays well below decomposition temperature of the reactive agent and below fluxing temperature of the resin particles, discharging the batch from the mixing chamber and cooling the discharged batch to avoid agglomeration of the resin particles.

U.S. Pat. No. 5,895,790 issued to Good, is directed to thermosetting a wide range of polymer blends. Briefly, a wide range of polymer blends and waste thermoset material can be recovered. One method of thermosetting a wide range polymer blends forms a homogenous and adaptable first method material. This material has a melt index of zero and a relatively predictable density. Very high levels of fibrous non-polymers may be added to the first method material.

U.S. Pat. No. 6,709,146 issued to Little, is directed to a thermokinetic mixer and method of using. Briefly, a thermokinetic mixer has a mixing chamber with shaft projections removable at least in part and replaceable without cutting the projections from the shaft. In another embodiment, only a tip portion of such projections are removable and replaceable without such cutting. In another embodiment, shaft projections into the mixing chamber include a tooth having a substantially reticulated face forming a deflecting surface such that substantially all mixing chamber particles encountering the tooth strike are deflected at an incident substantially lateral angle from the deflecting surface.

SUMMARY OF THE INVENTION

The present invention is directed to the application of the thermokinetic compounding (TKC) process in the field of pharmaceutical manufacturing, which offers numerous advantages such as brief processing times, low processing temperatures, high shear rates, and the ability to compound thermally incompatible materials into more homogenous composites. With these unique attributes, TKC offers a more efficient method of producing pharmaceutical compositions than traditional pharmaceutical processing operations, and in some instances permits the production of compositions that can not be achieved by conventional methods. Thus, the application of TKC to pharmaceutical manufacturing represents a substantial advance in terms of processing efficiency, compositional capabilities, as well as commercial viability of dosage forms of advanced formulation design, e.g. solid dispersions. Moreover, TKC is an entirely novel process to pharmaceutical manufacturing.

An embodiment of the present disclosure is directed to a method of making a pharmaceutical composition that includes one or more active pharmaceutical ingredients (API) with one or more pharmaceutically acceptable excipients by thermokinetic compounding by thermokinetic processing the one or more APIs with the one or more pharmaceutically acceptable excipients into a composite. The novel pharmaceutical composition or composite made by TKC may be further processed according to methods well known to those of skill in the art, including but not limited to hot melt extrusion, melt granulation, compression molding, tablet compression, capsule filling, film-coating, or injection molding into a final product. In certain embodiments, the composite made by TKC is the final product.

In one aspect, the composite is a homogenous, heterogenous, or heterogeneously homogenous composite or an amorphous composite. In another aspect, the thermokinetic processing may be conducted with or without a processing agent. Examples of processing agents include a plasticizer, a thermal lubricant, an organic solvent, an agent that facilitates melt blending, and an agent that facilitates downstream processing (e.g., lecithin). The thermokinetic processing may be conducted in a thermokinetic chamber. A thermokinetic chamber is an enclosed vessel or chamber in which TKC occurs. In one aspect, the average temperature inside the chamber is ramped up to a pre-defined final temperature over the duration of processing to achieve optimal thermokinetic mixing of the one or more APIs and the one or more pharmaceutically acceptable excipients into a composite. The length of processing and exposure to elevated temperatures during thermokinetic mixing will generally be below the thermal sensitivity threshold of the APIs, the excipients or both. The composite may also include a carrier, e.g., a polymer with a high melt viscosity. In another aspect, the release rate profile of the one or more APIs is determined by the one or more excipients of the composition. As such, the composition may be formulated for immediate release, mixed release, extended release or combinations thereof.

In another aspect, the particle size of the one or more APIs is reduced in an excipient/carrier system in which the APIs are not miscible, not compatible, or not miscible or compatible. In one aspect, the one or more APIs are a nanocomposite with the excipient, a carrier, or the excipient and a carrier. In another aspect, the thermokinetic processing is performed at an average temperature at or below the melting point of one or more of the APIs or excipients; the thermokinetic processing is performed at an average temperature at or below the glass transition temperature of one or more of the APIs or excipients; or the thermokinetic processing is performed at an average temperature at or below the molten transition point of one or more of the APIs or excipients.

In another aspect, the API may be a small organic molecule, protein, peptide, or polynucleic acid. The aqueous solubility of the API may be poorly soluble. Any pharmaceutically acceptable excipient known to those of skill in the art may be used to produce the composites and compositions disclosed herein. Examples of excipients for use with the present invention include, but are not limited to, e.g., a pharmaceutically acceptable polymer, a thermolabile polymeric excipient, or a non-polymeric exicipient. Other non-limiting examples of excipients include, lactose, glucose, starch, calcium carbonate, kaoline, crystalline cellulose, silicic acid, water, simple syrup, glucose solution, starch solution, gelatin solution, carboxymethyl cellulose, shellac, methyl cellulose, polyvinyl pyrrolidone, dried starch, sodium alginate, powdered agar, calcium carmelose, a mixture of starch and lactose, sucrose, butter, hydrogenated oil, a mixture of a quarternary ammonium base and sodium lauryl sulfate, glycerine and starch, lactose, bentonite, colloidal silicic acid, talc, stearates, and polyethylene glycol, sorbitan esters, polyoxyethylene sorbitan fatty acid esters, polyoxyethylene alkyl ethers, poloxamers (polyethylene-polypropylene glycol block copolymers), sucrose esters, sodium lauryl sulfate, oleic acid, lauric acid, vitamin E TPGS, polyoxyethylated glycolysed glycerides, dipalmitoyl phosphadityl choline, glycolic acid and salts, deoxycholic acid and salts, sodium fusidate, cyclodextrins, polyethylene glycols, polyglycolyzed glycerides, polyvinyl alcohols, polyacrylates, polymethacrylates, polyvinylpyrrolidones, phosphatidyl choline derivatives, cellulose derivatives, biocompatible polymers selected from poly(lactides), poly(glycolides), poly(lactide-co-glycolides), poly(lactic acid)s, poly (glycolic acid)s, poly(lactic acid-co-glycolic acid)s and blends, combinations, and copolymers thereof.

In another aspect, the method, compositions and composite of the present invention may be adapted for oral, rectal, vaginal, topical, urethral, otic, ocular, or transdermal administration. In one advantage of the present disclosure, the thermokinetic processing substantially eliminates API and excipient degradation. For example, in certain embodiments thermokinetic processing may generate compositions and composites with less than about 1.0%, 0.75%, 0.5%, 0.1%, 0.05%, or 0.01% degradation products of each API. This advantage is important for thermally labile APIs, which typically undergo significant degradation during thermal processing, as well as APIs that are subject to oxidation. In other embodiments, thermokinetic processing truly generate compositions with a minimum of at least about 90%, 91%, 92%, 93%, 94%, 95%, 96%, 97%, 98%, 99%, or 99.9% drug potency with respect to each API. Examples of thermokinetic processing may be performed for less than 5, 10, 15, 20, 25, 30, 35, 40, 45, 50, 55, 60, 75, 100, 120, 150, 180, 240 and 300 seconds. Generally, thermokinetic processing may be performed for between 5 and 120 seconds, 7 and 180 seconds, 10 to 60 seconds, 15 to 45 seconds, and 20 to 30 seconds. In one aspect, the API has amorphous, crystalline, or intermediate morphology.

Another embodiment of the present invention includes a method of processing a composite having one or more active pharmaceutical ingredients (API) with one or more pharmaceutically acceptable excipients by thermokinetic compounding, by thermokinetic processing the one or more APIs with the one or more pharmaceutically acceptable excipients into a composite. Another embodiment of the present invention includes a method of preprocessing a composite having one or more active pharmaceutical ingredients (API) with one or more pharmaceutically acceptable excipients by the thermokinetic compounding, by thermokinetic processing the one or more APIs with the one or more pharmaceutically acceptable excipients into a composite. The method may further include processing the composite by hot melt extrusion, melt granulation, compression molding, tablet compression, capsule filling, film-coating, or injection molding. In one aspect, the thermokinetic processing step does not include a processing agent. Examples of processing agents include those selected from the group consisting of a plasticizer, a thermal lubricant, an organic solvent, an agent that facilitates melt blending, and and an agent that facilitates downstream processing. The thermokinetic processing may be performed for less than 5, 10, 15, 20, 25, 30, 35, 40, 45, 50, 55, 60, 75, 100, 120, 150, 180, 240 and 300 seconds, and any ranges therein.

Yet another embodiment of the present invention includes a method of preplasticizing one or more pharmaceutical polymers by blending the polymers with one or more plasticizer selected from the group consisting of oligomers, copolymers, oils, organic molecules, polyols having aliphatic hydroxyls, ester-type plasticizers, glycol ethers, poly (propylene glycols), multi-block polymers, single block polymers, poly(ethylene oxides), phosphate esters; phthalate esters, amides, mineral oils, fatty acids and esters thereof with polyethylene glycol, glycerin or sugars, fatty alcohols and ethers thereof with polyethylene glycol, glycerin or sugars, and vegetable oils by thermokinetic mixing prior to agglomeration, by thermokinetic processing the one or more polymers with the one or more plasticizers into a composite. The method may further include the step of processing the composite with one or more APIs by hot melt extrusion, melt granulation, compression molding, tablet compression, capsule filling, film-coating, or injection molding. In one aspect, the method may further include preplasticizing the polymers and plasticizers with one or more excipients.

In yet another embodiment of the present invention, a method is used for dry milling one or more APIs by thermokinetic compounding to reduce the particle size of the API bulk material. In certain aspects, the API is crystalline. For example, by using this method, the particle size may be reduced to less than 1000 μm, 100 μm, 10 μm, or 1 μm. As described hereinabove, the thermokinetic mixing is performed for less than 5, 10, 15, 20, 25, 30, 35, 40, 45, 50, 55, 60, 75, 100, 120, 150, 180, 240 and 300 seconds, and any ranges therein.

In a further modification of the present invention, combinations of one or more APIs, one or more optional functional excipients and one or more immiscible carrier materials may be processed by thermokinetic mixing to produce nanocomposites in situ. Processing may be conducted for times ranging from 5 to 1000 seconds at processing speeds and durations either above, at, or below the thermal transition temperature. Additional processing may also be conducted to achieve a nanocomposites structure of the final product. Materials that may be used to generate nanocomposites include but are not limited to silica, talc, magnesium stearate, colloidal silicon dioxide, clay, glycerol monstearate, steric acid, and the like. Physical properties of pharmaceutical compositions that may be modified using thermokinetic mixing to achieve nanoconfinement are as follows:

(a) Pharmaceutical products with controlled drug release: The use of nanoconfinement may significantly increase the tortuosity of an API through dosage forms, e.g., controlled release dosage forms, by helping to control the diffusion pathways and therefore drug release rates.

(b) Pharmaceutical films with enhanced moisture transport properties: The use of nanoconfinement is contemplated to regulate physical properties of the composition to help control moisture uptake, thereby producing compositions with more desirable process performance.

(c) Pharmaceutical Materials with enhanced downstream processing characteristics: The use of nanoconfinement may provide enhanced mechanical properties, such as changes to elastic moduli, to facilitate downstream properties for tableting, encapsulation and other pharmaceutically acceptable dosage form development techniques known to those skilled in the art, e.g., injection molding, compression molding, film pressing, pelletizing, hot melt extrusion, melt granulation, tablet compression, capsule filling, and film-coating.

(d) Increased mechanical properties for pharmaceutical devices: The use of nanoconfinement may be able to provide enhanced mechanical properties, for example based on reduced relaxation events, particularly around physiological temperatures, which may allow the use of polymers that are not suitable for device applications due to mechanical issues, ranging from transdermal patches to medicated dental floss to implantable devices, to be applied in these applications. These enhanced mechanical properties may also lead to a longer lifetime for such devices and therefore reduced dosing frequency.

The present invention is also directed to the use of thermokinetic compounding, for example thermokinetic mixing until melt blended, to produce a composite of two or more pharmaceutically acceptable excipients that are immiscible by any other processing method known to those of skill in the art. In one aspect, the composite is a heterogeneously homogenous composite or an amorphous composite.

The present invention also includes a method of rendering a crystalline or semi-crystalline pharmaceutical polymer amorphous for an extended duration by thermokinetic compounding, for example thermokinetic mixing until melt blended. In one aspect of the present invention, the polymer is rendered amorphous for greater than 2 months, 6 months, 1 year, or 2 years when stored at, e.g., ambient conditions or the typical storage conditions for the API.

The present invention is also directed to pharmaceutical compositions comprising one or more active pharmaceutical ingredients with one or more pharmaceutically acceptable excipients wherein the composition is a homogenous, heterogenous, or heterogenously homogenous composition in which the glass transition temperature is significantly higher than the glass transition temperature of an identical formulation of identical active pharmaceutical ingredients and pharmaceutically acceptable excipients thermally processed, with or without use of a plasticizer. In other embodiments, the composition has a single glass transition temperature, wherein the identical formulation thermally processed has two or more glass transition temperatures. In still other embodiments, the pharmaceutical compositions have a single glass transition temperature that is at least about 20%, 30%, 40%, 50%, 60%, 70%, 80%, or 90% higher than the lowest glass transition temperature of the identical formulation thermally processed. The composition may be processed by thermokinetic compounding, and the identical formulation may be thermally processed according to methods known to those of skill in the art, including but not limited to hot melt extrusion, melt granulation, compression molding, tablet compression, capsule filling, film-coating, or injection molding.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
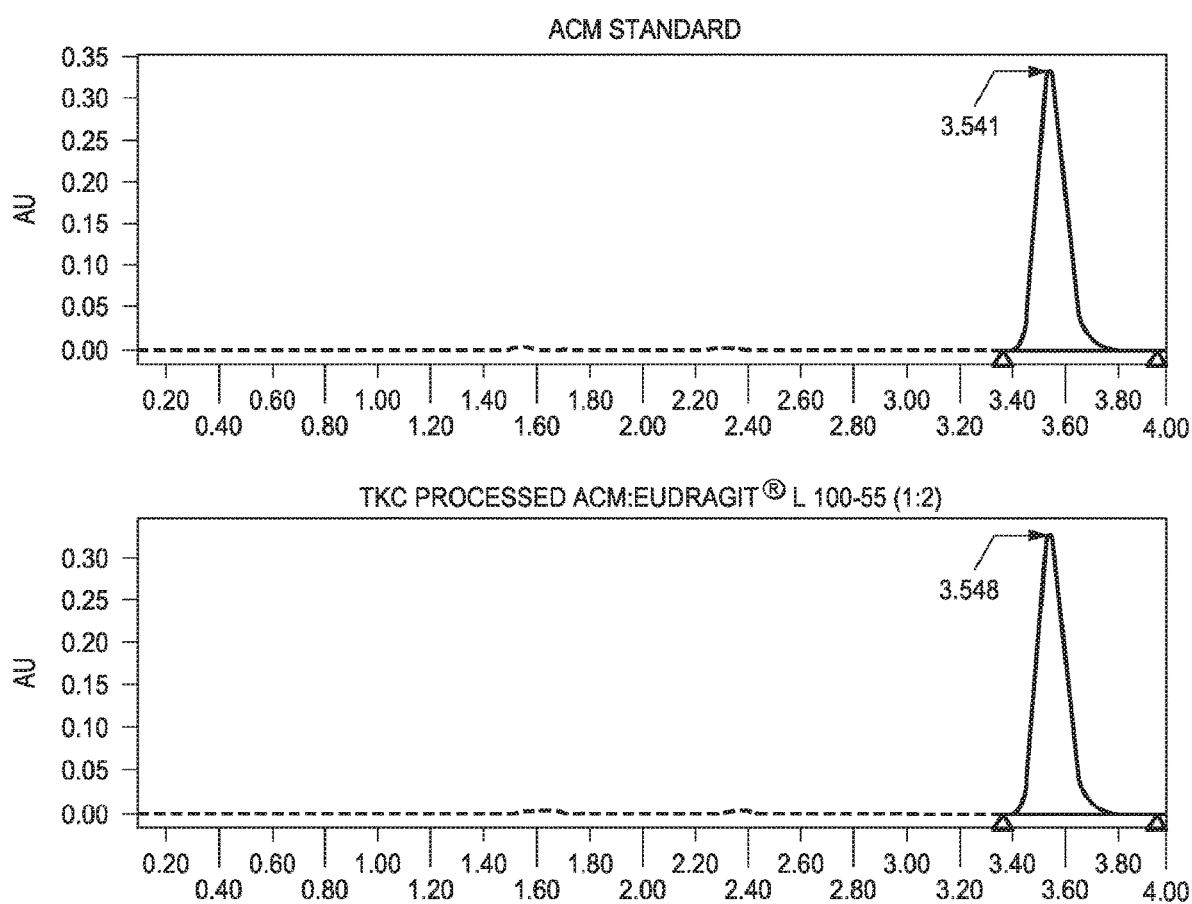
FIG. 1. HPLC analysis of ACM:EUDRAGIT® L 100-55 (1:2) TKC processed material as compared to an ACM standard injection.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "thermokinetic compounding" or "TKC" refers to a method of thermokinetic mixing until melt blended. TKC may also be described as a thermokinetic mixing process in which processing ends at a point sometime prior to agglomeration.

As used herein, the phrase "a homogenous, heterogenous, or heterogeneously homogenous composite or an amorphous composite" refers to the various compositions that can be made using the TKC method.

As used herein, the term "heterogeneously homogeneous composite" refers to a material composition having at least two different materials that are evenly and uniformly distributed throughout the volume.

Whether the composition is a homogenous, heterogenous, or heterogenously homogenous composition, an amorphous composition or combinations thereof, the TKC processing conditions can produce a composition with a glass transition temperature that is higher than the glass transition temperature of an identical formulation of identical active pharmaceutical ingredients (API) and pharmaceutically acceptable excipients thermally processed, for example either with or without the use of a plasticizer. The TKC processing conditions can also produce a composition with a single glass transition temperature, wherein an identical formulation of identical active pharmaceutical ingredients and pharmaceutically acceptable excipients, processed thermally, has two or more glass transition temperatures. In another example, the pharmaceutical compositions of the present disclosure have a single glass transition temperature that is at least about 20%, 30%, 40%, 50%, 60%, 70%, 80%, or 90% higher than the lowest glass transition temperature of the identical formulation processed thermally. Alternatively, the compositions made using thermokinetic processing may generate compositions with a minimum of at least about 90%, 91%, 92%, 93%, 94%, 95%, 96%, 97%, 98%, 99%, or 99.9% drug potency with respect to each API.

As used herein, the term "thermokinetic chamber" refers to an enclosed vessel or chamber in which the TKC method is used to make the novel compositions of the present invention. In a TKC chamber the average temperature inside the chamber is ramped up to a pre-defined final temperature over the duration of processing to achieve thermokinetic compounding of the one or more APIs and the one or more pharmaceutically acceptable excipients into a composite. The length of processing and exposure to elevated temperatures during thermokinetic compounding will generally be below the thermal sensitivity threshold of the APIs, the excipients or both. The pre-defined final temperature is selected to reduce the possibility that the one or more APIs, excipients and/or processing agents are degraded or their functionality is impaired during processing. Generally, the pre-defined final temperature, pressure, time of processing and other environmental conditions (e.g., pH, moisture, buffers, ionic strength, $O_2$) will be selected to substantially eliminate API, excipient and/or processing agent degradation.

As used herein, "bioavailability" is a term meaning the degree to which a drug becomes available to the target tissue after being administered to the body. Poor bioavailability is a significant problem encountered in the development of pharmaceutical compositions, particularly those containing an active ingredient that is not highly soluble. In certain embodiments such as formulations of proteins, the proteins may be water soluble, poorly soluble, not highly soluble, or not soluble. The skilled artisan will recognize that various methodologies may be used to increase the solubility of proteins, e.g., use of different solvents, excipients, carriers, formation of fusion proteins, targeted manipulation of the amino acid sequence, glycosylation, lipidation, degradation, combination with one or more salts and the addition of various salts.

As used herein, the phrase "pharmaceutically acceptable" refers to molecular entities, compositions, materials, excipients, carriers, and the like that do not produce an allergic or similar untoward reaction when administered to humans in general.

As used herein, "pharmaceutically acceptable carrier" or "pharmaceutically acceptable materials" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the pharmaceuticals compositions and composites disclosed herein is contemplated. Supplementary active ingredients can also be incorporated into the compositions and composites.

Examples of active pharmaceuticals ingredients (APIs) include, but are not limited to, antibiotics, analgesics, vaccines, anticonvulsants; antidiabetic agents, antifungal agents, antineoplastic agents, antiparkinsonian agents, antirheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents. In certain embodiments, the API is a poorly water-soluble drug or a drug with a high melting point.

The API may be found in the form of one or more pharmaceutically acceptable salts, esters, derivatives, analogs, prodrugs, and solvates thereof. As used herein, a "pharmaceutically acceptable salt" is understood to mean a compound formed by the interaction of an acid and a base, the hydrogen atoms of the acid being replaced by the positive ion of the base. Non-limiting examples of pharmaceutically acceptable salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate. Another method for defining the ionic salts may be as an acidic functional group, such as a carboxylic acid functional group, and a pharmaceutically acceptable inorganic or organic base. Non-limiting examples of bases include, but are not limited to, hydroxides of alkali metals such as sodium, potassium and lithium; hydroxides of calcium and magnesium; hydroxides of other metals, such as aluminum and zinc; ammonia; and organic amines, such as unsubstituted or hydroxy substituted mono-, di-, or trialkylamines; dicyclohexylamine; tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, "poorly soluble" refers to having a solubility such that the dose to be administered cannot be dissolved in 250 ml of aqueous media ranging in pH from 1 to 7.5, drugs with slow dissolution rates, and drugs with low equilibrium solubilities, for example resulting in decreased bioavailability or reduced pharmacological effect of the therapeutic agent being delivered.

As used herein, "derivative" refers to chemically modified inhibitors or stimulators that still retain the desired effect or property of the original API. Such derivatives may be derived by the addition, removal, or substitution of one or more chemical moieties on the parent molecule. Such moieties may include, but are not limited to, an element such as a hydrogen or a halide, or a molecular group such as a methyl group. Such a derivative may be prepared by any method known to those of skill in the art. The properties of such derivatives may be assayed for their desired properties by any means known to those of skill in the art. As used herein, "analogs" include structural equivalents or mimetics.

A variety of administration routes are available for delivering the APIs to a patient in need. The particular route selected will depend upon the particular drug selected, the weight and age of the patient, and the dosage required for therapeutic effect. The pharmaceutical compositions may conveniently be presented in unit dosage form. The APIs suitable for use in accordance with the present disclosure, and their pharmaceutically acceptable salts, derivatives, analogs, prodrugs, and solvates thereof, can be administered alone, but will generally be administered in admixture with a suitable pharmaceutical excipient, diluent, or carrier selected with regard to the intended route of administration and standard pharmaceutical practice.

The APIs may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot. As used herein, the term "parenteral" includes subcutaneous, intravenous, intramuscular, or infusion routes of administration.

The solution agent used in the solution can be an aqueous such as water, one or more organic solvents, or a combination thereof. When used, the organic solvents can be water miscible or non-water miscible. Suitable organic solvents include but are not limited to ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

The excipients and adjuvants that may be used in the presently disclosed compositions and composites, while potentially having some activity in their own right, for example, antioxidants, are generally defined for this application as compounds that enhance the efficiency and/or efficacy of the effective ingredients. It is also possible to have more than one effective ingredient in a given solution, so that the particles formed contain more than one effective ingredient.

As stated, excipients and adjuvants may be used to enhance the efficacy and efficiency of the APIs. Non-limiting examples of compounds that can be included in the solutions are cryoprotectants, lyoprotectants, surfactants, fillers, stabilizers, polymers, protease inhibitors, antioxidants and absorption enhancers. The excipients may be chosen to modify the intended function of the effective ingredient by improving flow, or bioavailability, or to control or delay the release of the API. Specific nonlimiting examples include: sucrose, trehaolose, Span 80, Tween 80, Brij 35, Brij 98, Pluronic, sucroester 7, sucroester 11, sucroester 15, sodium laurel sulfate, oleic acid, laureth-9, laureth-8, Lauric acid, vitamin E TPGS, Gelucire 50/13, Gelucire 53/10, Labrafil, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones and tyloxapol. Using the process of the present invention, the morphology of the effective ingredients can be modified, resulting in highly porous microparticles and nanoparticles.

Exemplary thermal binders that may be used in the presently disclosed compositions and composite include but are not limited to polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, and xanthan gum. One embodiment of the binder is poly(ethylene oxide) (PEO), which can be purchased commercially from companies such as the Dow Chemical Company, which markets PEO under the POLY OX™ trademark exemplary grades of which can include WSR N80 having an average molecular weight of about 200,000; 1,000,000; and 2,000,000.

Suitable grades of PEO can also be characterized by viscosity of solutions containing fixed concentrations of PEO, such as for example:

| POLYOX Water-Soluble Resin NF | Viscosity Range Aqueous Solution at 25° C., mPa · s |
|---|---|
| POLYOX Water-Soluble Resin NF WSR N-10 | 30-50 (5% solution) |
| POLYOX Water-Soluble Resin NF WSR N-80 | 55-90 (5% solution) |
| POLYOX Water-Soluble Resin NF WSR N-750 | 600-1,200 (5% solution) |
| POLYOX Water-Soluble Resin NF WSR-205 | 4,500-8,800 (5% solution) |
| POLYOX Water-Soluble Resin NF WSR-1105 | 8,800-17,600 (5% solution) |
| POLYOX Water-Soluble Resin NF WSR N-12K | 400-800 (2% solution) |
| POLYOX Water-Soluble Resin NF WSR N-60K | 2,000-4,000 (2% solution) |
| POLYOX Water-Soluble Resin NF WSR-301 | 1,650-5,500 (1% solution) |
| POLYOX Water-Soluble Resin NF WSR Coagulant | 5,500-7,500 (1% solution) |
| POLYOX Water-Soluble Resin NF WSR-303 | 7,500-10,000 (1% solution) |

Suitable thermal binders that may or may not require a plasticizer include, for example, Eudragit™ RS PO, Eudragit™ 100, Kollidon SR (poly(vinyl acetate)-co-poly (vinylpyrrolidone) copolymer), Ethocel™ (ethylcellulose), HPC (hydroxypropylcellulose), cellulose acetate butyrate, poly(vinylpyrrolidone) (PVP), poly(ethylene glycol) (PEG), poly(ethylene oxide) (PEO), poly(vinyl alcohol) (PVA), hydroxypropyl methylcellulose (HPMC), ethylcellulose (EC), hydroxyethylcellulose (HEC), sodium carboxymethyl-cellulose (CMC), dimethylaminoethyl methacrylate—methacrylic acid ester copolymer, ethylacrylate—methylmethacrylate copolymer (GA-MMA), C-5 or 60 SH-50 (Shin-Etsu Chemical Corp.), cellulose acetate phthalate (CAP), cellulose acetate trimelletate (CAT), poly(vinyl acetate) phthalate (PVAP), hydroxypropylmethylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30-D™ (MA-EA, 1:1), Eudragit L-100-55™ (MA-EA, 1:1), hydroxypropylmethylcellulose acetate succinate (HPMCAS), Coateric™ (PVAP), Aquateric™ (CAP), and AQUACOAT™ (HPMCAS), polycaprolactone, starches, pectins; polysaccharides such as tragacanth, gum arabic, guar gum, and xanthan gum.

The stabilizing and non-solubilizing carrier may also contain various functional excipients, such as: hydrophilic polymer, antioxidant, super-disintegrant, surfactant including amphiphillic molecules, wetting agent, stabilizing agent, retardant, similar functional excipient, or combination thereof, and plasticizers including citrate esters, polyethylene glycols, PG, triacetin, diethyiphthalate, castor oil, and others known to those or ordinary skill in the art. Extruded material may also include an acidifying agent, adsorbent, alkalizing agent, buffering agent, colorant, flavorant, sweetening agent, diluent, opaquant, complexing agent, fragrance, preservative or a combination thereof.

Exemplary hydrophilic polymers which can be a primary or secondary polymeric carrier that can be included in the composites or composition disclosed herein include poly (vinyl alcohol) (PVA), polyethylene-polypropylene glycol (e.g. POLOXAMER™), carbomer, polycarbophil, or chitosan. Hydrophilic polymers for use with the present invention may also include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. Hydrophilic polymers also include polyethylene oxide, sodium carboxymethycellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

By "immediate release" is meant a release of an active agent to an environment over a period of seconds to no more than about 30 minutes once release has begun and release begins within no more than about 2 minutes after administration. An immediate release does not exhibit a significant delay in the release of drug.

By "rapid release" is meant a release of an active agent to an environment over a period of 1-59 minutes or 0.1 minute to three hours once release has begun and release can begin within a few minutes after administration or after expiration of a delay period (lag time) after administration.

As used herein, the term "extended release" profile assumes the definition as widely recognized in the art of pharmaceutical sciences. An extended release dosage form will release the drug (i.e., the active agent or API) at a substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms).

By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered.

The term "controlled release", as regards to drug release, includes the terms "extended release", "prolonged release", "sustained release", or "slow release", as these terms are used in the pharmaceutical sciences. A controlled release can begin within a few minutes after administration or after expiration of a delay period (lag time) after administration.

A slow release dosage form is one that provides a slow rate of release of drug so that drug is released slowly and approximately continuously over a period of 3 hr, 6 hr, 12 hr, 18 hr, a day, 2 or more days, a week, or 2 or more weeks, for example.

The term "mixed release" as used herein refers to a pharmaceutical agent that includes two or more release profiles for one or more active pharmaceutical ingredients. For example, the mixed release may include an immediate release and an extended release portion, each of which may be the same API or each may be a different API.

A timed release dosage form is one that begins to release drug after a predetermined period of time as measured from the moment of initial exposure to the environment of use.

A targeted release dosage form generally refers to an oral dosage form that is designed to deliver drug to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can deliver to other sections of the gastrointestinal tract such as the stomach, jejunum, ileum, duodenum, cecum, large intestine, small intestine, colon, or rectum.

By "delayed release" is meant that initial release of drug occurs after expiration of an approximate delay (or lag) period. For example, if release of drug from an extended release composition is delayed two hours, then release of the drug begins at about two hours after administration of the composition, or dosage form, to a subject. In general, a delayed release is opposite of an immediate release, wherein release of drug begins after no more than a few minutes after administration. Accordingly, the drug release profile from a particular composition can be a delayed-extended release or a delayed-rapid release. A "delayed-extended" release profile is one wherein extended release of drug begins after expiration of an initial delay period. A "delayed-rapid" release profile is one wherein rapid release of drug begins after expiration of an initial delay period.

A pulsatile release dosage form is one that provides pulses of high active ingredient concentration, interspersed with low concentration troughs. A pulsatile profile containing two peaks may be described as "bimodal." A pulsatile profile of more than two peaks may be described as multi-modal.

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

The resulting composites or compositions disclosed herein may also be formulated to exhibit enhanced dissolution rate of a formulated poorly water soluble drug.

An example of a composition or formulation having a stable release profile follows. Two tablets having the same formulation are made. The first tablet is stored for one day under a first set of conditions, and the second tablet is stored for four months under the same first set of conditions. The release profile of the first tablet is determined after the single day of storage and the release profile of the second tablet is determined after the four months of storage. If the release profile of the first tablet is approximately the same as the release profile of the second tablet, then the tablet/film formulation is considered to have a stable release profile.

Another example of a composition or formulation having a stable release profile follows. Tablets A and B, each comprising a composition according to the invention, are made, and Tablets C and D, each comprising a composition not according to the invention, are made. Tablets A and C are each stored for one day under a first set of conditions, and tablets B and D are each stored for three months under the same first set of conditions. The release profile for each of tablets A and C is determined after the single day of storage and designated release profiles A and C, respectively. The release profile for each of tablet B and D is determined after the three months of storage and designated release profiles B and D, respectively. The differences between release profiles A and B are quantified as are the differences between release profiles C and D. If the difference between the release profiles A and B is less than the difference between release profiles C and D, tablets A and B are understood to provide a stable or more stable release profile.

Specifically, the TKC process can be used for one or more of the following pharmaceutical applications.

Dispersion of one or more APIs, wherein the API is a small organic molecule, protein, peptide, or polynucleic acid; in polymeric and/or non-polymeric pharmaceutically acceptable materials for the purpose of delivering the API to a patient via oral, pulmonary, parenteral, vaginal, rectal, urethral, transdermal, or topical routes of delivery.

Dispersion of one or more APIs, wherein the API is a small organic molecule, protein, peptide, or polynucleic acid; in polymeric and/or non-polymeric pharmaceutically acceptable materials for the purpose of improving the oral delivery of the API by improving the bioavailability of the API, extending the release of the API, targeting the release of the API to specific sites of the gastrointestinal tract, delaying the release of the API, or producing pulsatile release systems for the API.

Dispersion of one or more APIs, wherein the API is a small organic molecule, protein, peptide, or polynucleic acid; in polymeric and/or non-polymeric pharmaceutically acceptable materials for the purpose of creating bioerodable, biodegradable, or controlled release implant delivery devices.

Producing solid dispersions of thermolabile APIs by processing at low temperatures for very brief durations.

Producing solid dispersions of APIs in thermolabile polymers and excipients by processing at low temperatures for very brief durations.

Rendering a small organic API amorphous while dispersing in a polymeric, non-polymeric, or combination excipient carrier system.

Dry milling of crystalline API to reduce the particle size of the bulk material.

Wet milling of crystalline API with a pharmaceutically acceptable solvent to reduce the particle size of the bulk material.

Melt milling of a crystalline API with one or more molten pharmaceutical excipients having limited miscibility with the crystalline API to reduce the particle size of the bulk material.

Milling crystalline API in the presence of polymeric or non-polymeric excipient to create ordered mixtures where fine drug particles adhere to the surface of excipient particles and/or excipient particles adhere to the surface of fine drug particles.

Producing heterogeneously homogenous composites or amorphous composites of two or more pharmaceutical excipients for post-processing, e.g., milling and sieving, which are subsequently utilized in secondary pharmaceutical operations well known to those of skill in the art, e.g., film coating, tableting, wet granulation and dry granulation, roller compaction, hot melt extrusion, melt granulation, compression molding, capsule filling, and injection molding.

Producing single phase, miscible composites of two or more pharmaceutical materials previously considered to be immiscible for utilization in a secondary processing step, e.g. melt extrusion, film coating, tableting and granulation.

Pre-plasticizing polymeric materials for subsequent use in film coating or melt extrusion operations.

Rendering a crystalline or semi-crystalline pharmaceutical polymer amorphous, which can be used as a carrier for an API in which the amorphous character improves the dissolution rate of the API-polymer composite, the stability of the API-polymer composite, and/or the miscibility of the API and the polymer.

Deaggregate and disperse engineered particles in a polymeric carrier without altering the properties of the engineered particles.

Simple blending of an API in powder form with one or more pharmaceutical excipients.

Producing composites comprising one or more high melting point APIs and one or more thermolabile polymers without the use of processing agents.

Homogenously dispersing a coloring agent or opacifying agent within a polymer carrier or excipient blend.

Example 1

This study investigates the application of a novel manufacturing process, thermokinetic compounding (TKC), to the production of amorphous solid dispersion systems. The TKC process offers many of the same attributes that have made hot-melt extrusion (HME) a preferred method of manufacture for solid dispersions formulations. However, TKC has some very unique capabilities that distinguish the process from HME and suggest vast potential for innovative applications to various facets of pharmaceutical manufacturing. Specifically, TKC offers the benefits of very brief processing times, low processing temperatures, molten mixing without viscous flow, and significantly higher rates of shear than typical twin-screw melt extruders. It was the aim of this study to investigate the use of TKC for the production of amorphous pharmaceutical solid dispersion systems to assess its potential as an alternative technology to HME. Various solid dispersion systems were produced by TKC with different model drugs (acetaminophen (ACM), ketoconazole (KTZ) and indomethacin (IND)) and different polymeric carriers (Methocel™ E50, Kollidon® 30, and EUDRAGIT® L 100-55). Chromatographic analysis of solid dispersions of ACM and KTZ revealed no apparent degradation of these active agents by TKC processing. Differential scanning calorimetry (DSC) revealed that amorphous composites of KTZ in both Methocel™ E50 and Kollidon® 30 were achieved by TKC processing and these compositions had similar attributes to the same formulations processed by HME. Dissolution studies demonstrated extensive KTZ supersaturation in pH 6.8 phosphate buffer from an amorphous dispersion of KTZ, in Methocel™ E50 (1:2) produced by TKC. DSC revealed that substantially amorphous compositions of high melting point actives (KTZ and IND) in the thermolabile polymer EUDRAGIT® L 100-55 were produced by TKC processing without the addition of processing aids. The results of this study establish TKC as a novel technology for producing amorphous pharmaceutical solid dispersion systems. The unique attributes of TKC were shown to provide expanded manufacturing capabilities, which present innovative formulation opportunities for amorphous solid dispersion systems.

Examination of the Noyes-Whitney equation (Equation 1) (5) for the rate of solids dissolution reveals the method by which the dissolution properties of poorly water-soluble drug particles can be enhanced with formulation:

$$\frac{dC}{dt} = \frac{DA(C_s - C_t)}{h} \qquad (1)$$

dC/dt—Rate of solute dissolution
D—Diffusion coefficient
A—Effective surface area
$C_s$—Saturation concentration
$C_t$—Drug concentration at time t
h—Width of stagnant diffusion layer The total solute surface area (theoretical drug surface area) is increased via formulational methods by reducing drug particle size. An increase in total solute area may be accomplished by one of various techniques ranging from dry milling of drug crystals to the formation of solid solutions of drugs in excipient carriers. The formation of a solid solution represents the limit of particle size reduction as drug particles are divided and dispersed as individual molecules. Increasing the effective surface area, that portion of the total surface area which is in intimate contact with the solvent, is achieved with formulation by encapsulating drug particles/molecules in hydrophilic excipients. Hydrophilic encapsulation reduces the surface tension between the aqueous medium and the hydrophobic drug particles, thereby improving wettability and increasing the solvent surface coverage of the drug solute (6). Additionally, encapsulating particles in hydrophilic excipients decreases hydrophobic interactions between drug particles in aqueous media and thus reduces aggregation. It is seen from Equation 1 that the overall result of increasing the effective surface area (A) is a proportionate increase in the dissolution rate (dC/dt) of drug particles.

Altering the morphology of drug particles from the most thermodynamically stable crystalline form to a higher energy conformation (polymorph) accelerates dissolution by increasing the apparent saturation concentration ($C_s$) of the drug in the aqueous medium. Relating back to Equation 1, a greater $C_s$ value increases the solution saturation concentration gradient (Cs–Ct), thus providing a larger driving force for dissolution. Polymeric carriers in amorphous drug formulations can provide a stabilizing effect on supersaturated ITZ solutions, hence further increasing the apparent drug solubility and concurrently the overall dissolution rate. The utilization of polymers as stabilizers of supersaturated solutions is thus another method of improving the dissolution properties of poorly water-soluble drug molecules.

Solid dispersion technologies are widely used formulational techniques for improving the solubility characteristics of poorly water-soluble drugs. Each of the aforementioned modes of improving the dissolution properties of poorly soluble drug substances can be achieved simultaneously in the production of a solid dispersion formulation. For drug substances that are extremely insoluble, amorphous solid dispersion systems are often the only option for markedly improving dissolution rate owing to the thermodynamic stability of the crystal lattice structure (7). Numerous methods for the production of solid dispersions have been reported in the scientific literature; however, all of these methods are variations on either solvent or thermal treatment methods. Solvent techniques include such common processes as solvent evaporation (8), co-precipitation (9, 10), and spray drying (11), but also include more recently demonstrated techniques like cryogenic and supercritical fluid technologies (12, 13). Although the process details of these methods are quite different, the starting point is identical: the drug and the stabilizing excipients must be dissolved in a common solvent system. The end point of each of the processes is also identical: the solids must be recovered via solvent removal. These two commonalities are significant disadvantages of solvent-based solid dispersion processes. The use of solvents is costly, toxic to humans and the environment, and the requirement of common solubility of the drug and the excipients in the solvent system can be very restrictive with respect the excipients which can be used in the formulation (4, 14, 15). Additionally, solvent removal can be a lengthy process which reduces manufacturing efficiency. It is for these reasons that thermal methods of producing solid dispersion systems are preferred over solvent methods.

Early batch thermal methods involved heating the active and the carrier excipients in a vessel under agitation to a point where either the drug or the stabilizing excipient(s) or both were rendered molten (16-20). Owing to mixing and heating inefficiencies as well as prolonged heat exposure of the product, these early batch processes were not viable methods of producing solid dispersion systems on a large scale. With the application of hot-melt extrusion (HME) to the production of solid dispersion systems, problems of heating and mixing inefficiencies were remedied and the continuous nature of the process also improved the manufacturing efficiency (14, 21).

Numerous reports have been published in the pharmaceutical literature on the use of HME for the production of solid dispersion systems not only for the improvement of the dissolution properties of poorly water-soluble compounds, but also for the production of sustained release matrix systems (22-33). Although reports in the pharmaceutical literature and patents claiming the use of HME for pharmaceutical applications date back several decades, the commercial use of HME has been limited (4, 15). However, in recent years the utilization of HME for the production of commercial solid dispersion systems appears to be increasing. For example, Soliqs, a subsidiary of Abbott GmbH and Co. KG, is actively marketing a platform, HME-based drug delivery technology known as Meltrex™. The Meltrex™ system is the underlying technology utilized in the production of the new Kaletra® (lopinavir/ritonavir) tablet that replaced the former soft gelatin capsule formulation by providing a simpler more convenient anti-HIV drug therapy (34). The widely prescribed contraceptive NuvaRing® is another example of a recently commercialized solid dispersion formulation produced by HME. NuvaRing® is a sustained release etonogestrel/ethinyl estradiol ring-shaped vaginal insert which is rapidly growing in popularity due to its far more convenient dosing schedule over the more traditional tablet contraceptives. The 2006 U.S. sales for Kaltera® and NuvaRing® were 360 and 170 million (USD), respectively (35). These sales figures demonstrate the impact these products are having on their respective patient populations and in turn signify the emergence of HME as a viable commercial manufacturing process for the production of solid dispersion formulations.

Although HME may be one of the most viable methods of producing solid dispersion formulations, the process is not without a few critical limitations. Firstly, thermal incompatibility of drug substances and carrier excipients is a common problem encountered with HME processing of pharmaceutical formulations (14). What is meant by thermal incompatibility in this case is that the onset of thermal degradation of one of the formulation components is below the molten transition; i.e. glass transition temperature ($T_g$) or melting point ($T_m$), of another component. When amorphous compositions of ITZ in EUDRAGIT® L 100-55 and HP-55 were desired, the onset of degradation of these polymers was below the melting point of the drug and too near to the $T_g$s to process them by HME without the use of formulation additives. The inverse of this example, where the onset of degradation of the drug substance occurs below the $T_m$s or $T_g$s of the desired carrier excipients, is also a considerable obstacle to the utilization of HME in pharmaceutical manufacturing (36). When these thermal degradation issues are encountered, the most common solution is to reduce processing temperatures by lowering the temperature at which the molten transition of the carrier excipient(s) occurs. This is accomplished by the addition of plasticizing additives to the formulation. In another example, 20% triethyl citrate (TEC) was incorporated into the EUDRAGIT® L 100-55, HP-55, and EUDRAGIT® L 100-55/Carbopol 974P carrier systems to enable HME processing below the temperature at which thermal degradation of these polymers begins. In cases where thermal degradation is not a problem, plasticizers or thermal lubricants may still be required in order to reduce the melt viscosity of carrier excipients to facilitate molten flow of the formulation inside the extruder barrel. Particularly with high molecular weight polymers, the melt viscosity generates excessive load on the drive motor and precludes processing without the incorporation of additives to facilitate molten flow.

The importance of the glass transition temperature for long term stability of pharmaceutical solids is well known. Amorphous compositions have been well documented in the literature for the improved dissolution rates achieved in vitro and the enhanced bioavailabilities attained in vivo, however these compositions are thermodynamically unstable and the glass transition temperature has been indicated as a predictor of the solid state stability that can be attained for a composition. As a result of the thermodynamic instability of the system, these compositions will transition to the crystalline state over a given period of time, with the length of time dependent on the molecular mobility within the system. As the composition storage temperature increases, approaching the glass transition temperature, molecular mobility increases therefore it is recommended to develop compositions with a substantially higher glass transition temperature than the storage condition temperature to prevent recrystallization (15). Although plasticizers improve processing during melt extrusion, they also substantially lower the glass transition temperature which can reduce solid state stability of amorphous compositions. Production using TKC without the aid of the plasticizer results in compositions with substantially higher glass transition temperatures which can provide enhanced solid state stability.

The present inventors recognized that a problem associated with plasticization of polymeric carriers is in regard to amorphous solid dispersion systems and the reduction of the composite $T_g$. The addition of plasticizer to polymeric carriers reduces the $T_g$ of the matrix and promotes molecular mobility of the carrier and consequently recrystallization of amorphous drug dispersed within (37). The ultimate result is a dynamic drug release profile of the product on storage. Drug release which varies with storage time diminishes the safety and efficacy of drug products and therefore would preclude the marketability of formulations that lead to such instability.

These limitations of HME processing of pharmaceutical solid dispersion systems prompted the current study in which a novel process, thermokinetic compounding (TKC), was evaluated as a method of producing pharmaceutical solid dispersion systems. TKC is a derivative of thermokinetic mixing (TKM) which is an established, yet little known process in the polymer industry. It is used for blending additives like colorants, cellulose, graphite, clays, chemical agents (like foaming agents or fire retardants) and rubbers into polymers (38-40). The process is flexible and can blend materials with or without agglomeration (rendering the polymer molten) with varying degrees of effect. This flexibility is particularly useful when dispersing additives within heat sensitive polymers where thermal degradation is a significant issue. This flexibility is the primary advantage over its main competitive process, twin-screw extrusion compounding, which requires melting of the polymer. In cases where TKM is used for agglomeration, it has another advantage over twin-screw extrusion in that the materials are exposed to heat for much shorter durations. Additionally, TKM has been estimated to produce rates of shear much greater than twin-screw extrusion (39). When agglomeration is necessary, TKM has higher processing costs than twin-screw extrusion, so the polymer industry only uses it in very limited applications.

TKC is a unique, proprietary variation of TKM. The term thermokinetic compounding as used herein refers to thermokinetic mixing used for melt blending. TKS also refers to thermokinetic mixing which is stopped prior to agglomeration. One novel composition and method of the present disclosure is to change from a heat sensitive process to an aggressive heat intensive process focusing on agglomeration. The result of this novel process is that it compatibilizes vastly different polymers, e.g., thermoset (non-melting) polymers with thermoplastic (melting) polymers, as well as crystalline thermoplastics with highly amorphous thermoplastics. These compositions are not simply mixed by this process, but rather the two materials become bonded. Additionally, polymers with vastly different melting temperatures are able to be processed together without degrading the more heat-sensitive polymer. TKC processing times are brief (e.g., less than a minute) to minimize the heat exposure of compounded materials (active and/or non-active). With TKC, polymeric materials are rendered molten through mechanical generation of kinetic energy, not by the addition of external heat, and therefore molten processing can be achieved below the $T_g$ or $T_m$ of the polymeric materials. The process does not involve large-scale flow of molten material, and therefore overloading the drive motor as a result of high polymer melt viscosity is not a significant problem as with HME. These attributes of TKC provide substantial benefits over HME for pharmaceutical manufacturing applications.

TKC offers all of the same advantages of HME with respect to pharmaceutical manufacturing, e.g., non-solvent processing, providing intimate mixing of materials in the molten state, and highly efficient, scalable manufacturing. However, TKC has some very unique characteristics that may offer additional benefits to pharmaceutical manufacturing such as high shear rates, brief processing times that limit heat exposure of processing materials to just a few seconds, as well as the ability to process materials in their molten state at temperatures below their typical molten transitions. Processing molten polymers below their molten transition temperatures may enable the production of solid dispersion systems from thermally incompatible materials. As molten flow does not occur during TKC processing, processing additives such as plasticizers and thermal lubricants may not be necessary, which is another advantage over other manufacturing processes known in the art.

Based on the present findings, TKC processing has substantial applications to pharmaceutical manufacturing. The TKC process was used to produce amorphous solid dispersion formulations of poorly water-soluble drugs in various polymeric carriers, since it is believed that the attributes of the TKC apply particularly well to this aspect of pharmaceutical manufacturing. Firstly, as demonstrated herein, TKC is able to achieve the same result as melt extrusion with respect to producing amorphous solid dispersion systems of ketoconazole (KTZ) with thermally stable polymers. Secondly, as demonstrated herein, TKC offers certain advantages over HME by producing amorphous solid dispersions of high melting point drugs in the thermolabile EUDRAGIT™ L 100-55 polymer without the addition of plasticizers or other processing aids.

Materials and Methods. Ketoconazole, USP (KTZ) was purchased from Hawkins, Inc. (Minneapolis, Minn.). Acetaminophen, USP (ACM) was purchased from Fisher Scientific Co. (Houston, Tex.). Indomethacin, USP (IND) was purchased from Spectrum Chemical Mfg. Corp. (Gardena, Calif.), Kollidon® 30 PF (Povidone K 30 USP) was provided by BASF, (Ludwigshafen, Germany). Methocel™ E50 Premium LV (Hydroxypropyl methylcellulose 2910 50 cPs) were provided by The Dow Chemical Company, (Midland, Mich.). EUDRAGIT™ L 100-55 was purchased from Degussa GmbH (Linden, N.J.). HPLC grade Acetonitrile was purchased from EMD chemicals (Darmstadt, Germany). All other chemicals used in this study were of ACS grade.

Thermokinetic Compounding. One example of a thermokinetic compounder has a high horsepower motor driving the rotation of a horizontal shaft with teeth-like protrusions that extend outward normal to the rotational axis of the shaft. The portion of the shaft containing the protrusions is contained within an enclosed vessel where the compounding operation takes place, i.e., a thermokinetic chamber. The high rotational velocity of the shaft coupled with the design of the shaft protrusions imparts kinetic energy onto the materials being processed. Each processed batch contained the API and the polymer in a 1:2 (w/w) ratio with a total batch size of 1.36 kg. The batch size for the compounder used in this study is 3 to 4 kg; however, due to material cost, a much smaller batch size was used. The drug and polymer powders were accurately weighed, premixed in a bag, and loaded into the feed conduit as a blended powder. The compounder is operated by a digital control system which allows the operating parameters, i.e., revolutions per minute (RPM) and ejection temperature, to be set prior to the compounding operation. A temperature analyzer measures the average temperature inside the compounder vessel and in this case with small batch size, the temperature output was 20 to 40° C. lower than the skin temperature of the processed material owing to greater void volume in the vessel. The TKC machine can be run in automatic mode in which the digital control system ejects the material once the set temperature is reached within the vessel. For this study, material ejection was manually controlled and the temperature at the moment of ejection was recorded from the digital output. The skin temperature of the material was measured immediately following compounding using a Fluke 61 IR thermometer (Everett, Wash.). The operating parameters and skin temperatures of each compounded batch presented in this study are provided in Table 1.

TABLE 1

Operating parameters of the thermokinetic compounding process for each processed batch.

| Composition | RPM | Eject Temperature* (° C.) | Skin Temperature (° C.) |
|---|---|---|---|
| ACM:EUDRAGIT ® L100-55 (1:2) | 1950 | 66.1 | 88-93 |
| KTZ:Methocel ™ E50 (1:2) | 2000 | 95.6 | 150 |
| KTZ:Kollidon ® 30 (1:2) | 2000 | 77.2 | 140-150 |
| KTZ:EUDRAGIT ® L100-55 (1:2) | 1600 | 71.1 | 125 |
| KTZ:EUDRAGIT ® L100-55 (1:4) | 1600 | 71.1 | 90 |
| IND:EUDRAGIT ® L100-55 (1:2) | 1950 | 68.3 | 140 |
| IND:EUDRAGIT ® L100-55 (1:4) | 1600 | <65.6 | 60 |

*Eject temperature was measured by IR sensor as an average over the entire vessel volume. The eject temperature was lower than the actual product temperature due to the small batch size.

HPLC Analysis. All HPLC analysis presented in this study was conducted using a Waters (Milford, Mass.) high performance liquid chromatography (HPLC) system equipped with a photodiode array detector (Model 996), and an auto sampler (Model 717 Plus). The chromatographic data were collected and integrated using Empower® Version 5.0 software. The column used was a Phenomenex® Luna 5 µm C18(2) 100 A, 1150 mm×4.6 mm (Phenomenex®, Torrance, Calif.). The mobile phase for ACM consisted of 15:85 (v/v) acetonitrile:deionized water. The retention time of ACM was approximately 3.5 min with a flow rate of 1 mL/min. Chromatograms were extracted at 244 nm. For KTZ, the mobile phase consisted of 50:50 (v/v) acetonirtile: pH 6.8 phosphate buffer. The retention time of KTZ was approximately 6.1 min at a flow rate of 1.2 mL/min. Chromatograms were extracted at 225 nm.

Hot-Melt Extrusion (HME). The hot-melt extruded compositions presented in the DSC analysis of the KTZ:Methocel™ E50 (1:2) and KTZ:Kollidon® (1:2) TKC processed samples were produced with a HAAKE Minilab II Micro Compounder (Thermo Electron Corporation, Newington, N.H.) equipped with twin, co-rotating conical screws (5/14 mm diameter). All powder blends were fed into the extruder barrel via the Minilab manual feeding device. No external dye was applied at the outlet of the extruder barrel, and therefore extruded materials were forced through the 1.0× 4.0 mm rectangular outlet port. The operating parameters for both compositions presented were 170° C. and 300 RPM. After processing the extrudates were ground in a blade grinder (Capresso Inc., Closter, N.J.) for 2 minutes. The resulting ground product was then passed over a 60 mesh sieve. The material which passed through the sieve was manually milled in a porcelain mortar and pestle for 1 min to yield a fine powder. DSC analysis was then conducted on this finely milled powder.

Differential Scanning calorimetry (DSC). DSC analysis was conducted using a TA Instruments Model 2920 DSC (New Castle, Del.) equipped with a refrigerated cooling system. Samples were weighed to 15±5 mg in aluminum crimped pans (Kit 0219-0041, Perkin-Elmer Instruments, Norwalk, Conn.). For the KTZ dispersions in Methocel™ E50 and Kollidon® 30 the samples were heated at a ramp rate of 10° C./min from 5 to 215° C. with a modulation temperature amplitude of 0.5° C. and a modulation period of 40 seconds for all studies. For the IND and KTZ dispersions in EUDRAGIT® L 100-55 the samples were analyzed by conventional, non-modulated DSC at a ramp rate of 10° C./min from 5 to 200° C. Ultrahigh purity nitrogen was used as the purge gas at a flow rate of 40 mL/min. All data analyses were performed using TA Universal Analysis 2000 software. The thermogram for amorphous KTZ, used in the DSC analysis of the solid dispersions formulations of KTZ in Methocel™ E50 and Kollidon® 30 was obtained on a second heating of crystalline KTZ following an initial heating to 215° C. followed by rapid cooling (20° C./min) to 5° C. The thermograms of Methocel™ E50 and Kollidon® 30 were obtained by first run DSC following preheating of the polymer powders to 90° C. for 15 minutes in an MF-50 model moisture analyzer (AND Company Ltd. Encino, Calif.) to expel absorbed moisture.

Dissolution Testing. Dissolution testing of the TKC processed KTZ/Methocel™ E50 and KTZ/Kollidon® 30 formulations was performed according to USP 29 Apparatus 2 guidelines (paddle method) at 50 rpm in a Vankel 7000 Dissolution Tester (Vankel Technology Group, Cary, N.C.) equipped with a model VK 8000 auto sampler. The medium (900 mL pH 6.8 phosphate buffer) was degassed prior to use and maintained at 37±0.5° C. during testing. An amount of each tested formulation equivalent to 100 mg KTZ (~18 times saturation solubility) was added to each dissolution vessel (n=3). Aliquots of the dissolution media (5 mL) were sampled at 10, 20, 30, 60, 120, 180, 240, 360, and 1,440 minutes. All aliquots of dissolution media were filtered using Acrodisc® CR 13 mm syringe filters with a 0.2 µm PTFE membrane (Pall Life Sciences, East Hills, N.Y.). Filtered aliquots were then diluted in a 1:1 ratio with the KTZ HPLC mobile phase (described above). Sampled aliquots of dissolution media were analyzed for drug content by the KTZ HPLC method described previously. Area under the dissolution curve (AUDC) was calculated using the linear trapezoidal method.

Analysis of Drug Degradation in TKC Processed Compositions. To investigate the aggressive nature of the TKC process and its effect on the chemical stability of drug molecules, HPLC was performed on TKC processed compositions of ACM:EUDRAGIT® L 100-55 (1:2) and KTZ: Kollidon® 30 (1:2) to identify any significant degradation of these drug molecules which may have occurred during processing. For this analysis, six independent samples of the TKC processed ACM and KTZ compositions were evaluated by HPLC and compared to a pure drug standard. The results of this analysis for the ACM:EUDRAGIT® L 100-55 (1:2) formulations are shown in FIG. 1. Since each of the chromatograms obtained by HPLC analysis of the TKC material was identical, only a single representative chromatogram is provided in FIG. 1. It is seen in this figure that the representative chromatogram of the TKC processed samples is identical to the ACM standard. A single, well-defined peak with a retention time of 3.54 minutes representing the elution of ACM from the column is seen in the chromatogram representing the TKC processed samples. Each sample injection was evaluated for 8 minutes; however, the reported figures were truncated at about 4 minutes as there were no absorption peaks beyond the primary ACM peak. Degradation of ACM would be identified by the appearance of additional peaks to the primary ACM standard peak or by changes in the retention time or shape of the ACM peak. Since neither of these was observed, it was concluded that no significant degradation of ACM occurred during TKC processing.

Figure 2:
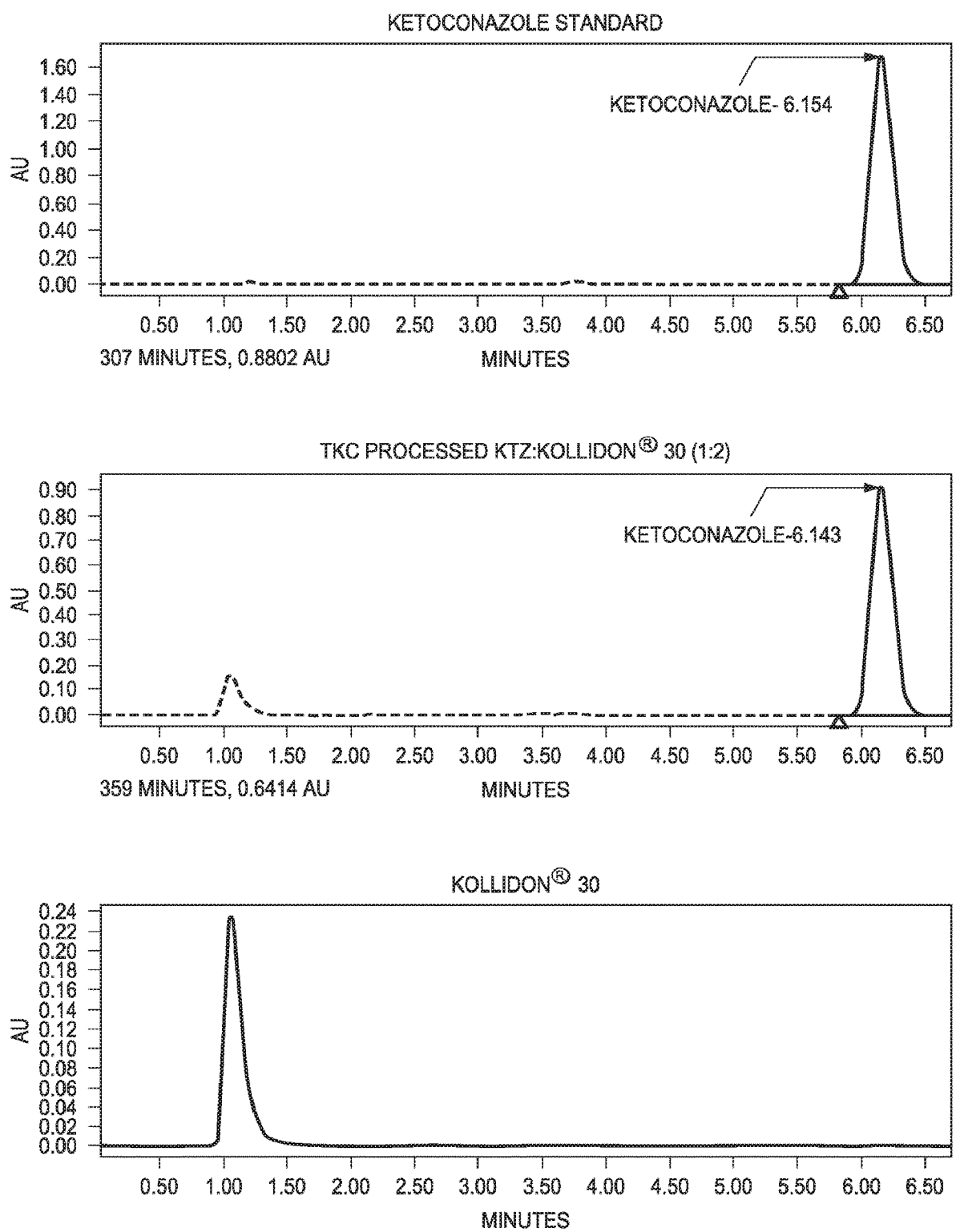
FIG. 2. HPLC analysis of KTZ:Kollidon® 30 (1:2) TKC processed material in comparison to a KTZ standard injection and the Kollidon® 30 polymer alone.

A similar result for the KTZ:Kollidon® 30 (1:2) composition is presented in FIG. 2. The representative chromatogram of the TKC processed samples shown in this figure is identical to the KTZ standard with the exception of a single peak eluting at about 1.2 minutes. This secondary peak is the result of the Kollidon® 30 polymer as can be seen by the polymer peak shown in the last row of FIG. 2. A well-defined peak with a retention time of about 6.1 minutes representing the elution of KTZ from the column is seen in the chromatogram representing the TKC processed samples. Each sample injection was evaluated for 10 minutes; however, the reported figures were truncated at about 6.5 minutes as there were no absorption peaks beyond the primary KTZ peak. Since no large unknown peaks or any apparent changes in the primary KTZ peak were observed by chromatographic analysis, it was concluded that degradation of KTZ did not result from TKC processing.

DSC Analysis of TKC Processed Compositions with Thermally Stable Polymers. With the aim of demonstrating the application of TKC for the production of amorphous solid dispersion formulations, KTZ was processed with two thermally stable polymers, Methocel™ E50 and Kollidon® 30. Immediately following processing the KTZ:Methocel™ E50 composition had the appearance of a large agglomerated mass with a skin temperature of 150° C. (as determined by IR thermometer) and a rubber-like consistency. The skin temperature of the compounded product at the moment of exit (150° C.) is a good indication that the compounded materials did not experience temperatures more than a few degrees above the melting point of KTZ (151° C.) during processing. Moreover, the processing time was approximately 10 seconds and since the material temperature increases with processing time, the compounded mass only momentarily experienced elevated temperatures.

Figure 3:
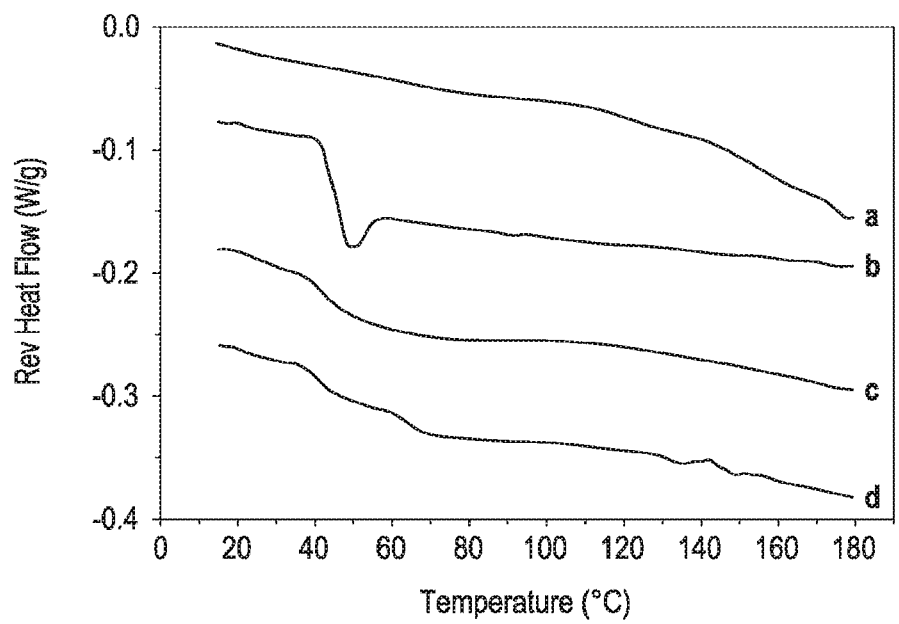
FIG. 3. Modulated DSC analysis of: (a) Methocel™ E50, (b) amorphous KTZ, (c) TKC processed KTZ:Methocel™ E50 (1:2), and (d) HME processed KTZ:Methocel™ E50 (1:2) at 170° C. and 300 RPM.

DSC analysis was conducted on the KTZ:Methocel™ E50 (1:2) TKC processed composition to determine the morphology of KTZ in the composite as well its dispersed state in the polymer. The Methocel™ E50 unprocessed polymer, amorphous KTZ, and a KTZ:Methocel™ E50 (1:2) HME processed composition (170° C./300 RPM) were also included in the analysis for comparison. It can be seen in FIG. 3 that Methocel™ E50 is a completely amorphous polymer with a very slight molten transition that appears to begin at about 140° C. This transition is very subtle and the sample size constraint of the utilized DSC system precludes adequate resolution of this event (41). Amorphous KTZ is seen in this figure to have a $T_g$ of approximately 45° C. The absence of thermal events indicating recrystallization or melting reveals the stability of the amorphous state of KTZ. The TKC processed KTZ:Methocel™ E50 (1:2) composition appears to be a single phase system as indicated by the single broad $T_g$ with midpoint at about 45° C.; however, the equivalence of this $T_g$ to that of amorphous KTZ suggests that this transition is the result of amorphous domains of KTZ distributed in the Methocel™ E50 matrix. If a molecular dispersion of KTZ in Methocel™ E50 were achieved, the $T_g$ of the composite would be expected to lie between the $T_g$ of KTZ and that of the polymer. The broadening of the KTZ $T_g$ is the result of mixing interactions between the amorphous drug domains and the polymer on heating during the DSC experiment. A similar distribution of itraconazole (ITZ) in hypromellose after HME processing was reported by Six et al. in which the composition contained separate drug and polymer-rich phases (41).

DSC analysis of the HME processed KTZ:Methocel™ E50 (1:2) sample revealed that a much more heterogeneous dispersion was produced by HME than TKC. Two distinct low-temperature transitions are seen at approximately 40° C. and 66° C. which may indicate the presence of amorphous domains of KTZ (40° C.) as well as domains of molecularly dispersed KTZ in Methocel™ E50 (66° C.). Also, what appears to be an exotherm (peak at ~145° C.) followed by an endotherm (minimum at ~150) may represent further phase separation of a small amount of KTZ from the polymer matrix during the DSC experiment.

In summary, the results of this DSC analysis demonstrate that a completely amorphous dispersion of KTZ domains in Methocel™ E50 was produced by TKC processing with similar dispersion properties as those reported by previous researchers for similar systems produced by HME. Additionally, it was revealed that a more homogenously dispersed system was achieved with TKC processing than with HME processing.

Figure 4:
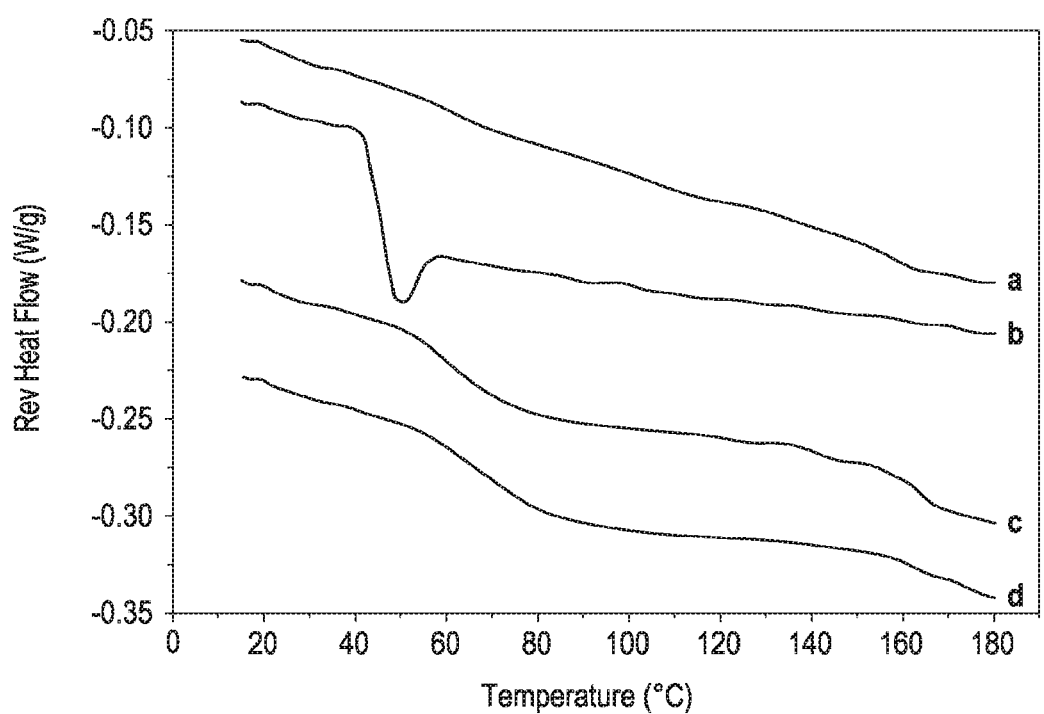
FIG. 4. Modulated DSC analysis of: (a) Kollidon® 30, (b) amorphous KTZ, (c) TKC processed KTZ:Kollidon® 30 (1:2), and (d) HME processed KTZ:Kollidon® 30 (1:2) at 170° C. and 300 RPM.

The TKC processing time of the KTZ:Kollidon® 30 (1:2) formulation was approximately 10 seconds and skin temperatures of the molten material were measured in the range of 140 to 150° C. As before, the processed materials experienced temperatures near the melting point of KTZ only for a very brief duration. Upon exit from the compounder the KTZ:Kollidon® 30 (1:2) formulation had the appearance of a uniform molten mass, white to yellow in color. DSC analysis was conducted on this TKC processed composite as well as the Kollidon® 30 unprocessed polymer and amorphous KTZ to determine the morphology and the dispersed state of KTZ in the polymer. Also, a KTZ:Kollidon® 30 (1:2) HME processed composition (170° C./300 RPM) was included in the analysis for a comparative evaluation of the two processes. The results of DSC analysis are presented in FIG. 4.

Similarly to Methocel™, the Kollidon® 30 polymer has a very subtle thermal transition with only a gradual downward slope indicating a steady increase in heat capacity of the polymer with increasing temperature. A very slight increase in downward slope appears in the 150 to 160° C. temperature range followed by a short plateau which may indicate the completion of the polymer's molten transition. Again, the glass transition of amorphous KTZ is shown in this figure at 45° C. to enable comparison with the $T_g$s of the TKC and HME processed samples. The thermograms of TKC and HME processed KTZ:Kollidon® 30 (1:2) compositions show the same general characteristics, i.e., they both demonstrate complete amorphousness of KTZ with a broad $T_g$ ranging between 50 and 80° C. The greater $T_g$ of the KTZ:Kollidon® composite than that of amorphous KTZ demonstrates the miscibility of the drug in the polymer as their intermolecular interactions lead to plasticization of Kollidon® while having the opposite effect on amorphous KTZ. Comparing this result to the previous KTZ:Methocel™ E50 composition, it is clear that KTZ is substantially more miscible with povidone than with hypromellose.

Although the thermograms of the TKC and HME processed KTZ:Kollidon® 30 (1:2) compositions appear similar, closer evaluation reveals a difference in the distribution of KTZ in the polymer. The calculated midpoints of the broad $T_g$s observed with both the TKC and HME processed samples were 61° C. and 67° C., respectively. The lower midpoint of the TKC processed sample indicates regions of the analyzed sample that are more rich in KTZ content which causes the $T_g$ to shift downward toward that of pure amorphous KTZ. The TKC processed sample also shows an obvious secondary thermal transition with onset near 160° C. that may indicate a polymer rich region of the sample. Such a transition is not as apparent with the HME processed composition. Considering these events together, it appears that the TKC processed KTZ:Kollidon® 30 (1:2) formulation is somewhat heterogeneous in comparison to the HME sample as there appears to be drug rich and polymer rich regions within a very small sample of the processed mass. This result may be attributable to the size and aggressiveness of the TKC machine utilized in this study. The TKC machine used in this study is designed for aggressive compounding to compatibilize dissimilar waste plastics by imparting high frictional and shear forces on the materials. The capabilities of this particular machine with respect to melt compounding therefore far exceed the requirements of this study. Therefore, the machine was operated at very low RPM relative to normal operation and run times were extremely brief. Additionally, as mentioned before the batch size used in the study was 2 to 3 times lower than the ideal batch. All of these factors result in a non-ideal mixing profile within the machine which likely contributed to the two phase composition seen with the KTZ:Kollidon® 30 (1:2) formulation. Microscopic heterogeneity was not detected by DSC analysis for the Methocel™ formulation because molecular mixing that would produce a $T_g$ shift was not achieved with this composition. Homogenous mixing of KTZ and Kollidon® 30 would be improved by increasing processing time; however, given the aggressive nature of the TKC machine utilized in this study more ideal processing times of 20 to 30 seconds were not possible as they would lead to polymer degradation. The future development of TKC for pharmaceutical applications will involve the modification of the machine design to allow for modulation of the aggressiveness of compounding to accommodate a number of different pharmaceutical applications and to allow for longer processing times to ensure composite homogeneity.

Figure 5:
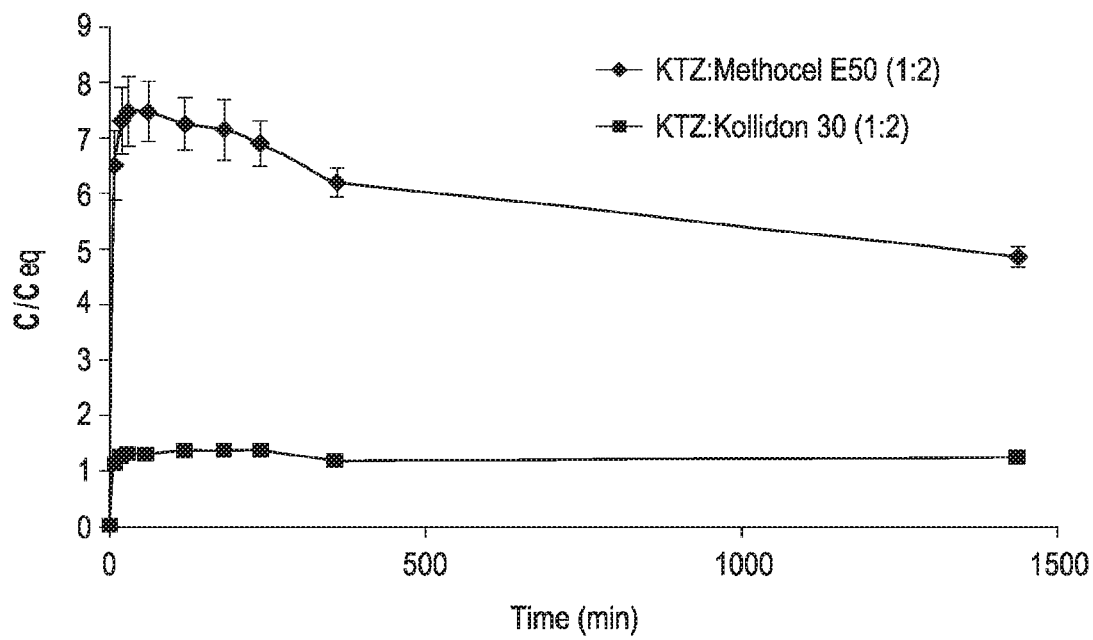
FIG. 5. Supersaturation dissolution testing of TKC processed KTZ:Methocel™ E50 and KTZ:Kollidon® 30 in 900 mL pH 6.8 phosphate buffer (37±0.2) by USP 29 Apparatus II Method at 50 RPM. To each dissolution vessel (n=3) 300 mg of each composition (100 mg KTZ equivalent) was added resulting in a 111 μg/mL KTZ theoretical complete dissolution concentration. This concentration is 18.6 times the equilibrium solubility of KTZ in neutral pH media (5.98 μg/mL) (42). The standard deviation for the KTZ:Kollidon® (1:2) formulation is too slight to be viewed in the figure due to the magnitude of the $C/C_{eq}$ scale.

Dissolution Testing of TKC Processed KTZ in METHOCEL™ E50 and KOLLIDON® 30. Supersaturation dissolution testing in pH 6.8 phosphate buffer was conducted on the KTZ:Methocel™ E50 (1:2) and KTZ:Kollidon® 30 (1:2) TKC processed samples to evaluate the extent of KTZ supersaturation achieved with these two formulations. The results of this study are presented in FIG. 5. The concentration of KTZ in solution at each time point was normalized by the saturation solubility of KTZ in neutral pH media (5.98 μg/mL (42)) in order to provide a more direct representation of supersaturation. In FIG. 5 it can be seen that the KTZ:Methocel™ E50 (1:2) and KTZ:Kollidon® 30 (1:2) formulations exhibit rapid dissolution rates, reaching 87% and 82% of their respective maximum concentrations in the first 10 minutes. However, the KTZ:Methocel™ E50 (1:2) formulation produced much more extensive supersaturation as indicated by a maximum $C/C_{eq}$ value of 7.6, as compared to the KTZ:Kollidon® 30 (1:2) formulation which showed a maximum $C/C_{eq}$ value of only 1.4. The duration of supersaturation with the KTZ:Methocel™ E50 (1:2) formulation was also found to far exceed that of the KTZ:Kollidon® 30 (1:2) formulation as indicated by their respective 24 hour $C/C_{eq}$ values of 4.9 and 1.2, respectively. The total area under the dissolution curve (AUDC) for the KTZ:Methocel™ E50 (1:2) and KTZ:Kollidon® 30 (1:2) formulations were determined to be 852 and 177 μg·hr/mL, respectively. These AUDC values are a clear indication of the superior stabilization of supersaturated concentrations of KTZ provided by Methocel™ E50 over Kollidon® 30. The same result was achieved with supersaturated concentrations of itraconazole (ITZ). This was attributed to stronger intermolecular interactions between ITZ and Methocel™ than with Kollidon® owing to the presence of free hydroxyl groups (hydrogen bonding sies) on Methocel™ which stabilize ITZ in solution. Since KTZ is also a weak base and molecularly very similar to ITZ, this mechanism of stabilization is likely the cause for the discrepancy in supersaturation observed between the two formulations investigated in this study. Correlating these in vitro results to the in vivo counterpart indicates that greater supersaturation of KTZ in the intestinal tract and hence greater absorption would be achieved with the Methocel™ E50 formulation over the Kollidon® 30 formulation. These results thus indicate the potential impact of TKC with regard to improving oral drug therapies with poorly water-soluble drugs.

Production of Solid Dispersion Systems by TKC with a Thermolabile Polymeric Carrier. As discussed previously, TKC has the capability of processing polymers in their molten states below their rigid-to-molten transition temperatures. It was also discussed above that a substantial limitation of HME processing is the required use of additives when thermal degradation and/or molten flow restricts processing. Therefore, it was the aim of this study to demonstrate the use of TKC to produce amorphous solid dispersion systems of KTZ and indomethacin (IND) in the thermolabile polymer EUDRAGIT® L 100-55 without the use of processing agents such as plasticizers or thermal lubricants. The successful production of these compositions demonstrates a substantial benefit of TKC processing over HME processing.

Two batches of KTZ:EUDRAGIT® L 100-55 with differing drug:polymer ratios (1:2) and (1:4), were processed by TKC. The texture of the material upon exiting the compounder was similar to the previously described samples, i.e. rubbery agglomerated mass. The skin temperature of the two compounded batches was measured to be 125° C. and 90° C. for the KTZ:EUDRAGIT® L 100-55 (1:2) and (1:4) batches, respectively. These temperatures are significant because they are below the $T_g$ of EUDRAGIT® L 100-55 (127° C.), below the melting point of KTZ (151° C.), and below the onset of degradation of EUDRAGIT® L 100-55 (~150° C.) (43). As before, processing times were brief (~10 seconds) and the processed materials were only momentarily exposed to elevated temperatures. Again, the size and aggressiveness of the compounder used in this study limited control of the energy imparted on the compounded materials, and as a result portions of the processed batches showed obvious signs of polymer degradation. However, there were also large portions of the processed batches which showed no signs of degradation and these portions were collected for further analysis. A smaller scale machine with more flexible operating parameters will be used in future studies in order to provide more precise process control so as to minimize intrabatch variations.

Figure 6:
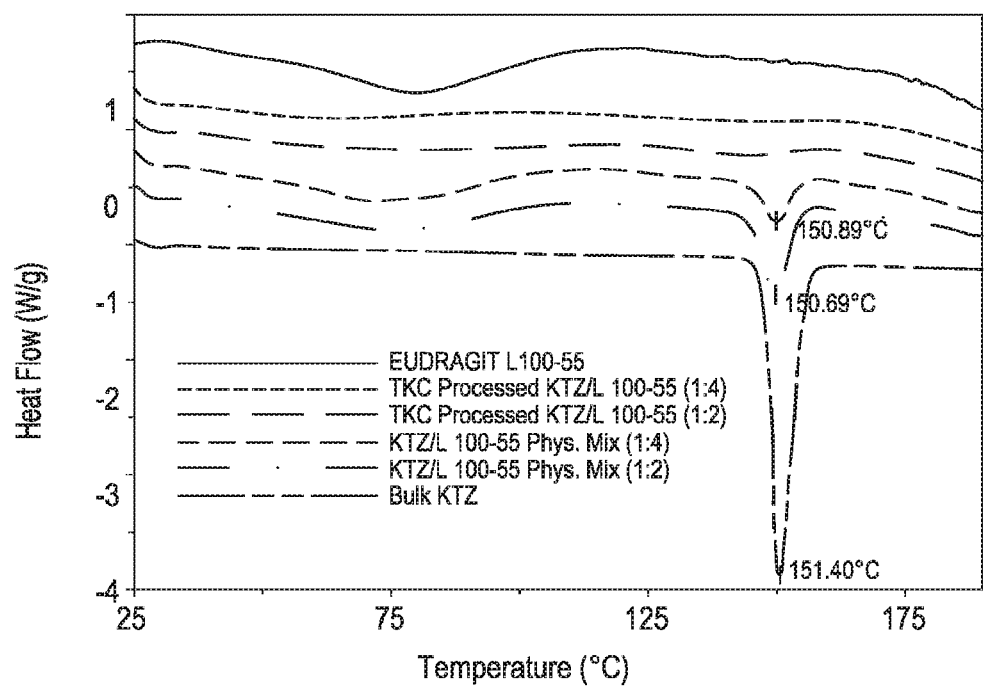
FIG. 6. DSC analysis of the TKC processed KTZ:EUDRAGIT® L 100-55 (1:4) and (1:2).

In FIG. 6, the DSC thermograms of both KTZ:EUDRAGIT® L 100-55 TKC processed batches are shown along with the unprocessed polymer, drug:polymer simple mixtures, and bulk KTZ for comparison. The thermogram for the KTZ:EUDRAGIT® L 100-55 (1:4) batch demonstrates that KTZ in this formulation was rendered entirely amorphous by TKC processing as indicated by the absence of the melting endotherm for crystalline KTZ at approximately 151° C. as seen in the corresponding simple mixture. A very slight amount of crystalline KTZ was detected in the KTZ:EUDRAGTT® L 100-55 (1:2) batch as indicated by the very shallow and broad endotherm occurring in the same range as the melting event of crystalline KTZ in the simple mixture. Although slight crystallinity was detected for this batch, the composition represents a substantial reduction in the crystallinity of KTZ as compared to the corresponding simple mixture.

Both KTZ:EUDRAGIT® L 100-55 batches were processed substantially below the melting point of KTZ, yet TKC processing was able to transform the drug from its native crystalline structure into an amorphous form. Moreover, the dispersion of KTZ into EUDRAGIT® L 100-55 was achieved without the use of plasticizers or other processing agents. Previously, it was found that the addition of 20% triethyl citrate was required to successfully process an ITZ:EUDRAGIT® L 100-55 (1:2) formulation due to temperature restrictions and the excessive melt viscosity of unplasticized EUDRAGIT® L 100-55. A disadvantage of the presence of large amounts of plasticizers in a solid dispersion system is that it can reduce the stability of the system and alter drug release profiles. Hence, the capability of TKC to produce an amorphous composition from thermally incompatible materials (a high melting point drug and a thermolabile polymer) without the use of processing aids indicates a substantial advantage of TKC over HME for the production of amorphous solid dispersion systems.

Compositions of IND in EUDRAGIT® L100-55 were also processed by TKC to study the effect with a different drug molecule. The melting point of IND is 161° C. and therefore the production of amorphous dispersions of IND with EUDRAGIT® L100-55 by thermal methods is also restricted by the aforementioned problems of polymer degradation. As with the previous KTZ formulations, two IND batches were processed in drug to polymer ratios of (1:4) and (1:2). Both products exited the compounder as molten agglomerated masses with a slight yellow color. The skin temperatures of the IND:EUDRAGIT® L100-55 (1:4) and (1:2) batches were 60 and 140° C., respectively.

Figure 7:
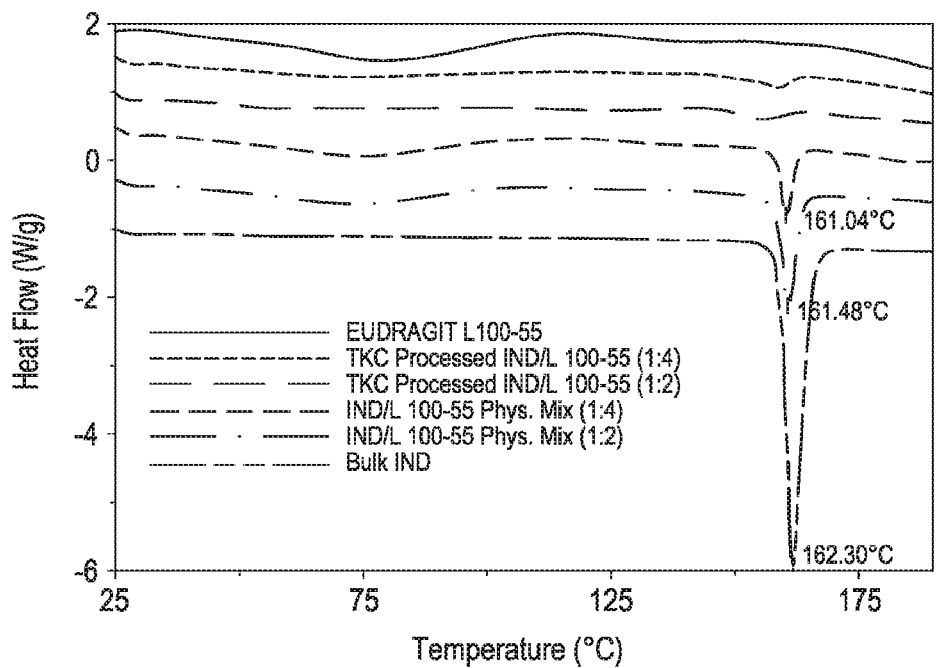
FIG. 7. DSC analysis of the TKC processed IND:EUDRAGIT® L 100-55 (1:4) and (1:2).

The thermograms for the IND:EUDRAGIT® L100-55 batches are shown in FIG. 7 along with unprocessed EUDRAGIT® L100-55 polymer, simple mixtures, and bulk IND for comparison. It is seen in this figure that both TKC processed batches contain IND in a substantially amorphous form. The IND:EUDRAGIT® L100-55 (1:4) batch appears to have slightly greater crystalline drug content than the IND:EUDRAGIT® L100-55 (1:4) batch which is evident by the sharper melting endotherm at approximately 161° C. This can be attributed to the difference in processing conditions between the two batches; i.e. reduced RPM (1600 vs. 1950) and lower skin temperature (60° C. vs. 140° C.) for the 1:4 versus the 1:2 batch. However, despite processing at much "colder" conditions, the drug content of the IND: EUDRAGIT® L100-55 (1:4) batch was rendered substantially amorphous by TKC processing. In both cases, the temperature of the material was substantially lower than the melting point of IND indicating that an amorphous dispersion of IND in EUDRAGIT® L 100-55 can be produced by TKC below the drug's melting point without the use of processing aids.

The slight crystallinity observed with these two IND: EUDRAGIT® L100-55 batches again can be attributed to the use of the large compounder with the relatively small batch sizes. Precise control is required to render the polymer molten and the drug amorphous without degrading EUDRAGIT® L100-55. However, such control is not possible with the large compounder and thus the batches were processed conservatively so as not to degrade the polymer. The result of conservative operation of the compounder was slight IND crystallinity in both processed batches.

In summary, the results of this study demonstrate the capability of TKC processing to form amorphous compositions from thermally incompatible materials, e.g. high melting point drugs with thermolabile polymers. As most poorly water-soluble drugs have high melting temperatures, the application of TKC processing for the production of amorphous solid dispersion systems will allow for greater flexibility in formulation as thermolabile polymers such as EUDRAGIT® L 100-55 can be utilized as carriers without the need for processing aids. Additionally, by eliminating the need for processing agents such as plasticizers and/or thermal lubricants, TKC processing can be utilized to produce more stable solid dispersion formulations and formulations with drug release characteristics that are not influenced by additives. Therefore, by enabling molten processing at temperatures below the melting points and glass transition temperatures of both the carrier and active materials, TKC processing represents a substantial advancement in manufacturing technology for solid dispersion systems.

Example 2

A further study provides a demonstration that amorphous solid dispersions of poorly water soluble drugs can be produced using a novel high energy manufacturing technology, thermokinetic compounding (TKC), having equivalent properties to compositions produced by hot melt extrusion (HME) with substantially reduced processing times.

Solid dispersions of poorly water soluble drugs, itraconazole (ITZ) and griseofulvin (GRIS), in hydrophilic carriers (1:2 drug:carrier ratio), hydroxypropyl methylcellulose and polyvinylpyrollidone, were produced using a novel high energy manufacturing process and compared to equivalent formulations processed by HME. Modulated differential scanning calorimetry (mDSC) and X-ray diffraction (XRD) were used to assess the amorphous nature of the compositions. Supersaturated dissolution testing was conducted by adding an amount of drug equivalent to 10-times equilibrium solubility to evaluate the degree and extent of supersaturation. Potency testing was performed by dissolving a known quantity of drug product in a suitable solvent and measuring the concentration of drug substance. Assay and dissolution samples were analyzed by HPLC.

Supersaturated dissolution testing was performed based on the USP XXIX apparatus II dissolution test using a VK 7010 dissolution apparatus (Varian, Inc., Palo Alto, Calif.) and VK 8000 autosampler (Varian, Inc., Palo Alto, Calif.). An equivalent amount of 10×0.1N HCl media equilibrium solubility was weighed and added to the dissolution vessel containing 900 mL of 0.1N HCl media. During testing 5 mL samples were removed from the dissolution vessels without replacement after 5, 10, 15, 30, 45 and 60 min. Samples were immediately filtered, diluted in a 1:1 ratio with mobile phase, vortexed mixed and transferred into 1 mL vials (VWR International, West Chester, Pa.) for analysis.

Griseofulvin dissolution samples were analyzed using a Waters (Waters Corporation, Milford, Mass.) high performance liquid chromatography (HPLC) system consisting of dual Waters 515 Syringe Pumps, a Waters 717 Autosampler and a Waters 996 Photo Diode Array extracting at a wavelength of 293.4 nm. The system was operated under isocratic flow at 1 mL/min using a mobile phase consisting of 60:35:5 water:acetonitrile:tetrahydrofuran equipped with a Phenomenex Luna CN 100 Å, 250 mm×4.6 mm (Phenomenex®, Torrance, Calif.) HPLC column. Data were collected and analyzed using Empower® Version 5.0 software.

Figure 8:
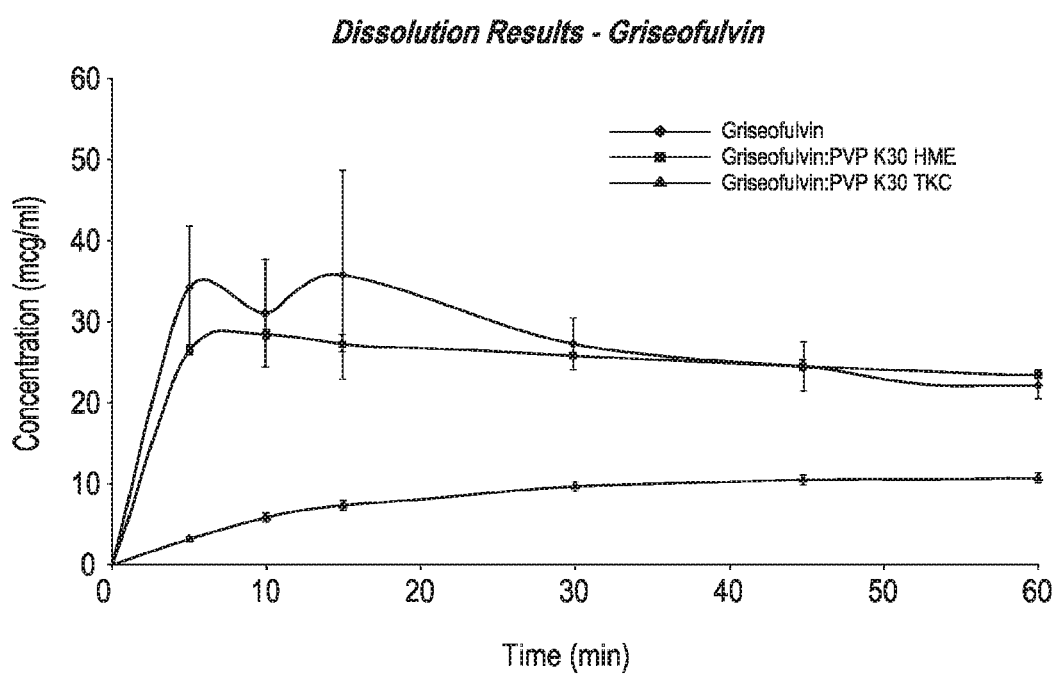
FIG. 8. Dissolution analysis of griseofulvin:PVP K30 processed by TKC and by HME.
Figure 9:
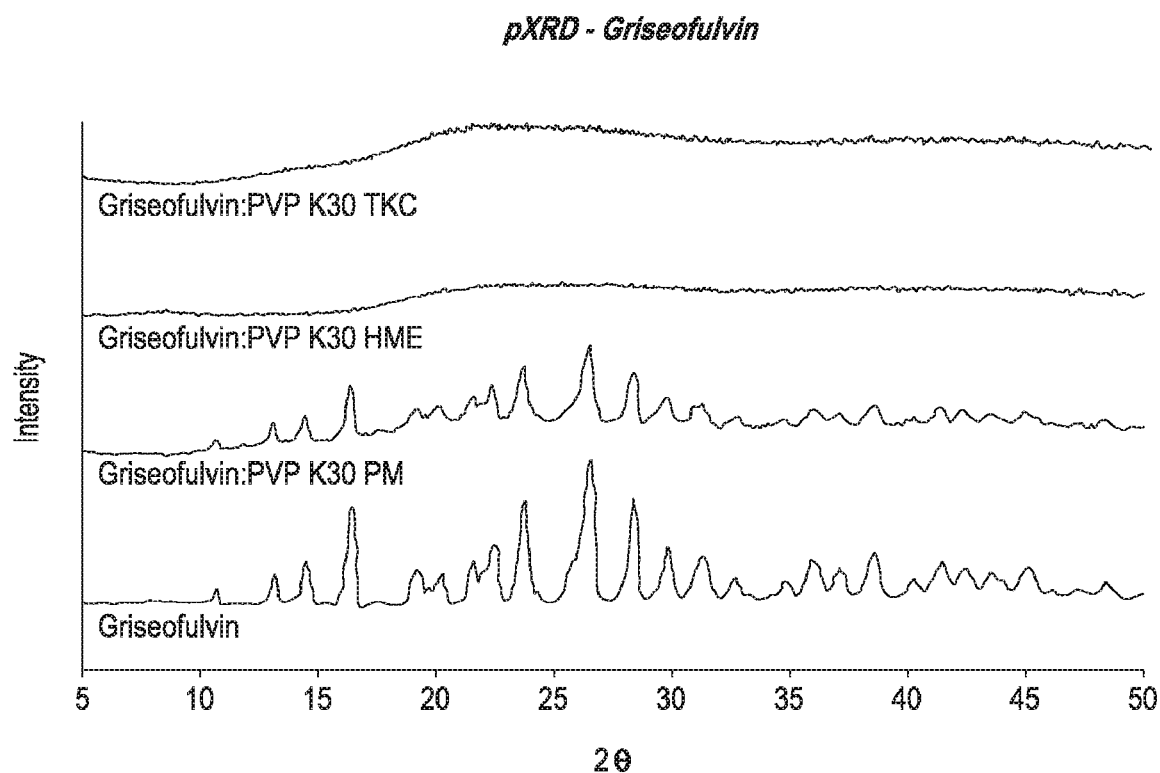
FIG. 9. pXRD analysis of griseofulvin:PVP K30 processed by TKC and by HME.

Supersaturated dissolution testing results for griseofulvin: PVP prepared by TKC and by HME are shown in FIG. 8. The compositions exhibited substantially faster dissolution rates than unprocessed drug substance. Furthermore, TKC processed compositions exhibited the ability to supersaturate media, offering the potential for enhanced bioavailability.

pXRD testing was conducted using a Philips Model 1710 X-ray diffractometer (Philips Electronic instruments Inc., Mahwah, N.J.). Samples of powder were placed into channeled stages and the diffraction profile was measured from 5° to 50° using a 2θ step size of 0.05° and dwell time of 3 s. The results of pXRD testing of griseofulvin:PVP K30 processed by TKC and by HME are shown in FIG. 9. Results for the mixture and for griseofulvin in powder form are also shown for comparison.

pXRD testing is used to evaluate the crystal structure of a material. Unprocessed griseofulvin exhibits several characteristic peaks indicative of its crystallinity, which are also present in physical mixtures of griseofulvin and PVP. These peak are absent in compositions of griseofulvin and PVP processed by TKC and HME, indicating that material processed in both forms is amorphous.

Modulated Differential scanning calorimetry testing for the griseofulvin products was performed using a TA Instruments Model 2920 DSC (New Castle, Del.) and analyzed using TA Universal Analysis 2000 Software. Samples were accurately weighed to 15±2 mg in aluminum crimped pans. Testing was performed at a ramp rate of 10° C./min. from 5 to 275° C. using a modulation temperature amplitude of 0.5° C. and a modulation period of 40 s under nitrogen purge at a flow rate of 40 mL/min. Drug free compositions were heated a minimum of 50 C above the glass transition temperature.

Figure 10:
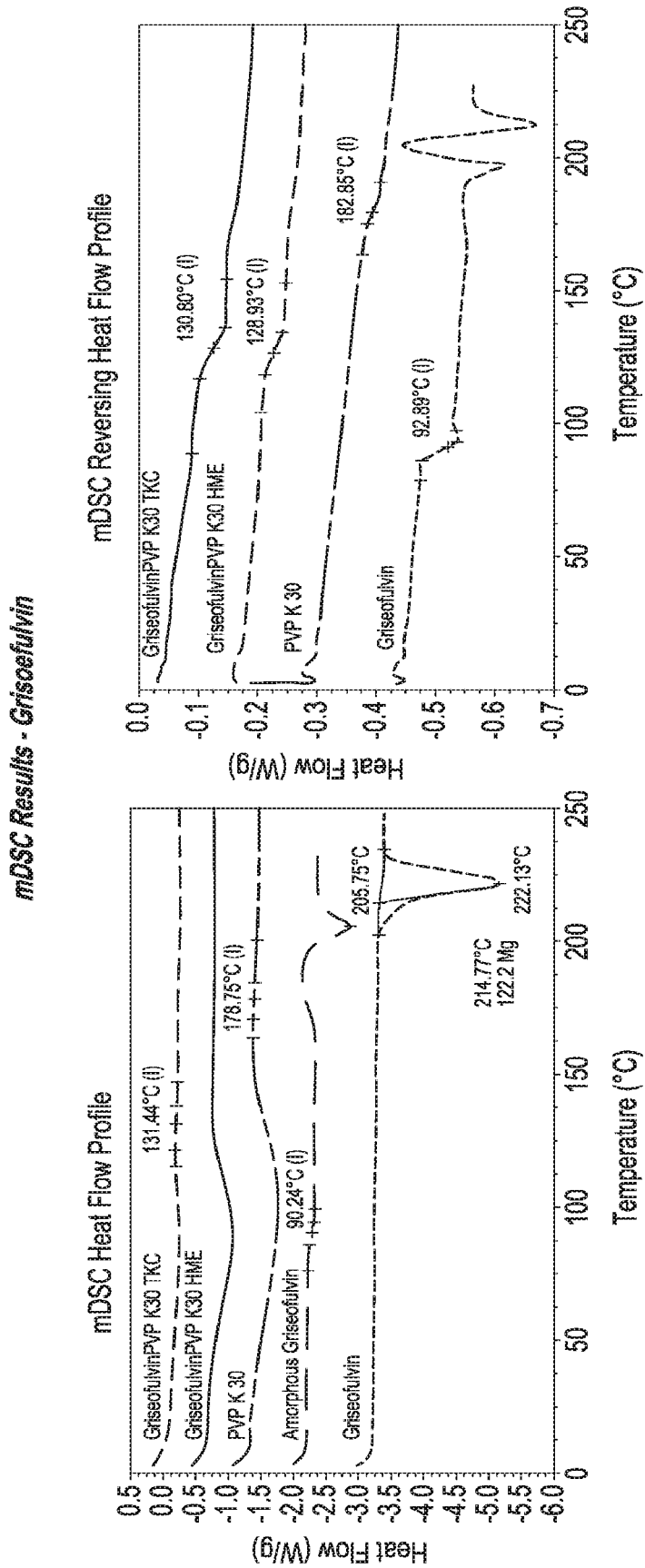
FIG. 10. DSC analysis of griseofulvin:PVP K30 processed by TKC and by HME.

Using mDSC testing it is possible to assess crystallinity and glass transition of a composition. The results of mDSC testing are shown in FIG. 10. Examination of the heat flow profile shows that griseofulvin exhibits a melting endotherm at 222° C. Formation of an amorphous composition formed by a quench cool of the 1st run sample, exhibits a characteristic griseofulvin glass transition temperature at 90° C. Later down stream events associated with recrystallization and melting can also be seen in the thermogram. Heat flow profiles for the PVP K30 composition, as well as for griseofulvin:PVP K30 compositions, do not exhibit melting endotherms, confirming the amorphous results seen in pXRD testing. Reversing heat flow profiles were examined to determine material glass transition values. PVP K30 compositions exhibited a glass transition temperature of 180° C., while the amorphous griseofulvin glass transition value was confirmed at 90° C. Compositions of griseofulvin:PVP K30 processed by both HME and TKC exhibited only a single glass transition phase at approximately 127°-130° C., indicating that both compositions existed as only a single phase.

Thus, solid dispersions prepared by TKC exhibited processing times under one minute, while processing of equivalent HME compositions required run times in excess of ten minutes. XRD testing of the solid dispersions produced by both TKC and HME showed an absence of crystalline peaks in the diffraction pattern, indicating an amorphous composition. mDSC testing of all compositions demonstrated the absence of drug substance melting endotherms, supporting the amorphous nature of the drug products. Furthermore, only a single glass transition temperature for TKC processed was observed for the composition indicating that the material was dispersed at a molecular level. Solid dispersions of ITZ and GRIS produced by TKC also exhibited excellent product potencies, with values ranging from 95.0%-105.0% of theoretical. Dissolution testing results showed that amorphous compositions had significantly higher dissolution rates than the crystalline drug substance, indicating potential for improved bioavailability.

Thus, TKC processed material exhibited similar physical and chemical properties compared to compositions produced by HME, and were produced with significantly shorter processing times. These results indicate that TKC is an effective and efficient method for producing pharmaceutically acceptable solid dispersions, offering substantially higher throughput than traditional HME processes.

Example 3

The inventors have also demonstrated that solid dispersions of itraconazole (ITZ) and Eudragit® L100-55 can be produced using a fusion process without the aid of a plasticizer to achieve superior solid state characteristics compared to material produced using traditional manufacturing techniques.

In this study, solid dispersions of ITZ and Eudragit® L100-55 (1:2) were produced using TKC and compared to equivalent formulations processed by hot melt extrusion (HME). HME processed material could not be produced without the aid of a plasticizer. Triethyl citrate (TEC) was used as a plasticizer at 20% w/w of dry polymer. Modulated differential scanning calorimetry (mDSC) and X-ray diffraction (XRD) were used to assess the amorphous nature of the compositions. Supersaturated dissolution testing was conducted based on the USP Method A enteric test by adding an amount of drug equivalent to 10-times acid phase equilibrium solubility to evaluate the degree and extent of supersaturation. Potency testing was performed by dissolving a known quantity of drug product in a suitable solvent. Potency and dissolution samples were analyzed by HPLC.

Supersaturated dissolution testing of itraconazole:HPMC E5 processed by TKC and by HME was performed based on the USP XXIX apparatus II dissolution test using a VK 7010 dissolution apparatus (Varian, Inc., Palo Alto, Calif.) and VK 8000 autosampler (Varian, Inc., Palo Alto, Calif.). An equivalent amount of 10×0.1N HCl media equilibrium solubility was weighed and added to the dissolution vessel containing 900 mL of 0.1N HCl media. During testing 5 mL samples were removed from the dissolution vessels without replacement after 5, 10, 15, 30, 45 and 60 min. Samples were immediately filtered, diluted in a 1:1 ratio with mobile phase, vortexed mixed and transferred into 1 mL vials (VWR International, West Chester, Pa.) for analysis.

Dissolution samples were analyzed using a Waters (Waters Corporation, Milford, Mass.) high performance liquid chromatography (HPLC) system consisting of dual Waters 515 Syringe Pumps, a Waters 717 Autosampler and a Waters 996 Photo Diode Array extracting at a wavelength of 263 nm. The system was operated under isocratic flow at 1 mL/min using a mobile phase consisting of 70:30:0.05 acetonitrile:water:diethanolamine equipped with a Phenomenex Luna 5 mcm C18(2) 100 Å, 150 mm×4.6 mm (Phenomenex®, Torrance, Calif.) HPLC column. Data were collected and analyzed using Empower® Version 5.0 software.

Figure 11:
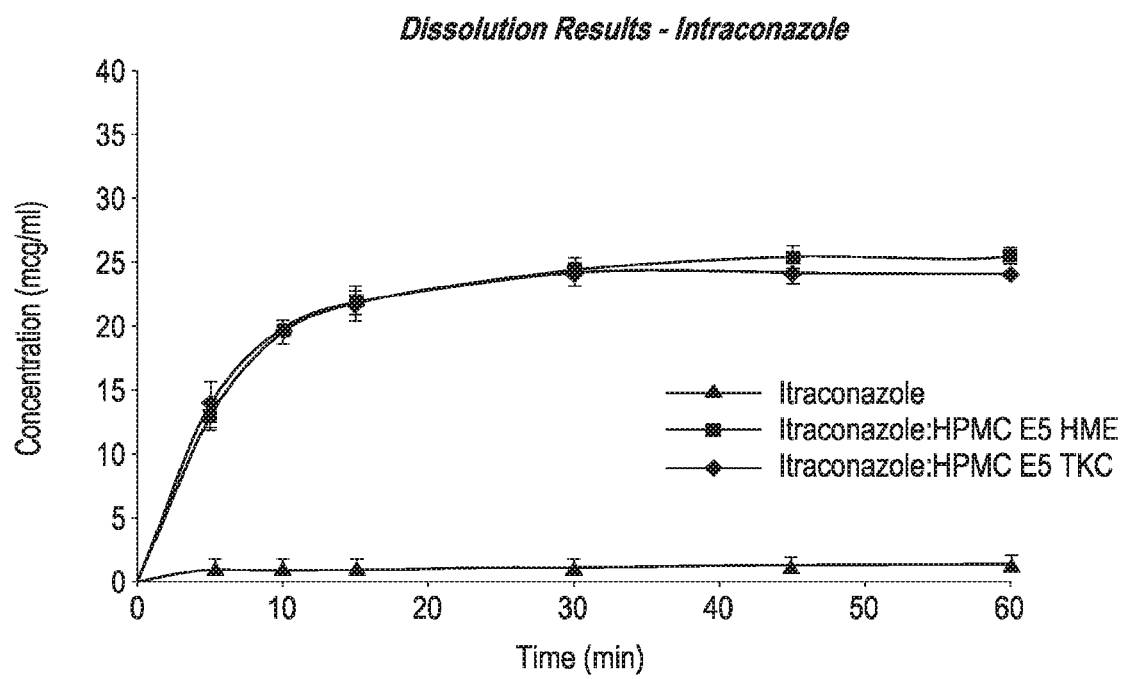
FIG. 11. Dissolution analysis of itraconazole:HPMC E5 processed by TKC and by HME.

Dissolution testing results are shown in FIG. 11. Itraconazole:HPMC solid dispersions produced by TKC and HME exhibited significantly higher dissolution rates with the capability of supersaturating. Additionally, no statistically significant difference was observed between manufacturing processes. This indicates that compositions produced by HME or TKC should provide equivalent bioavailabilities in vivo.

Figure 12:
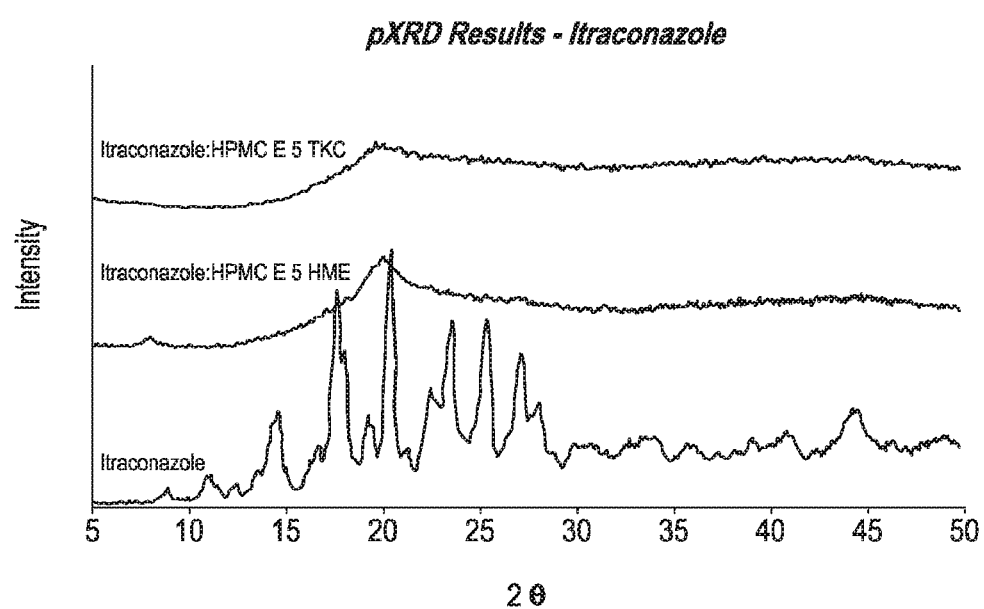
FIG. 12. pXRD analysis of itraconazole:HPMC E5 processed by TKC and by HME.

XRD testing of the itraconazole:HPMC E5 processed by TKC and by HME was conducted using a Philips Model 1710 X-ray diffractometer (Philips Electronic Instruments Inc., Mahwah, N.J.). Samples of powder were placed into channeled stages and the diffraction profile was measured from 5° to 50° using a 2θ step size of 0.05° and dwell time of 3 s. Result of the XRD testing is shown in FIG. 12.

XRD testing is used to evaluate the crystal structure of a material. Unprocessed itraconazole exhibits several characteristic peaks indicative of its crystallinity. These peak are absent in compositions of itraconazole and HPMC processed by TKC and HME, indicating that material processed in both forms is amorphous.

Figure 13:
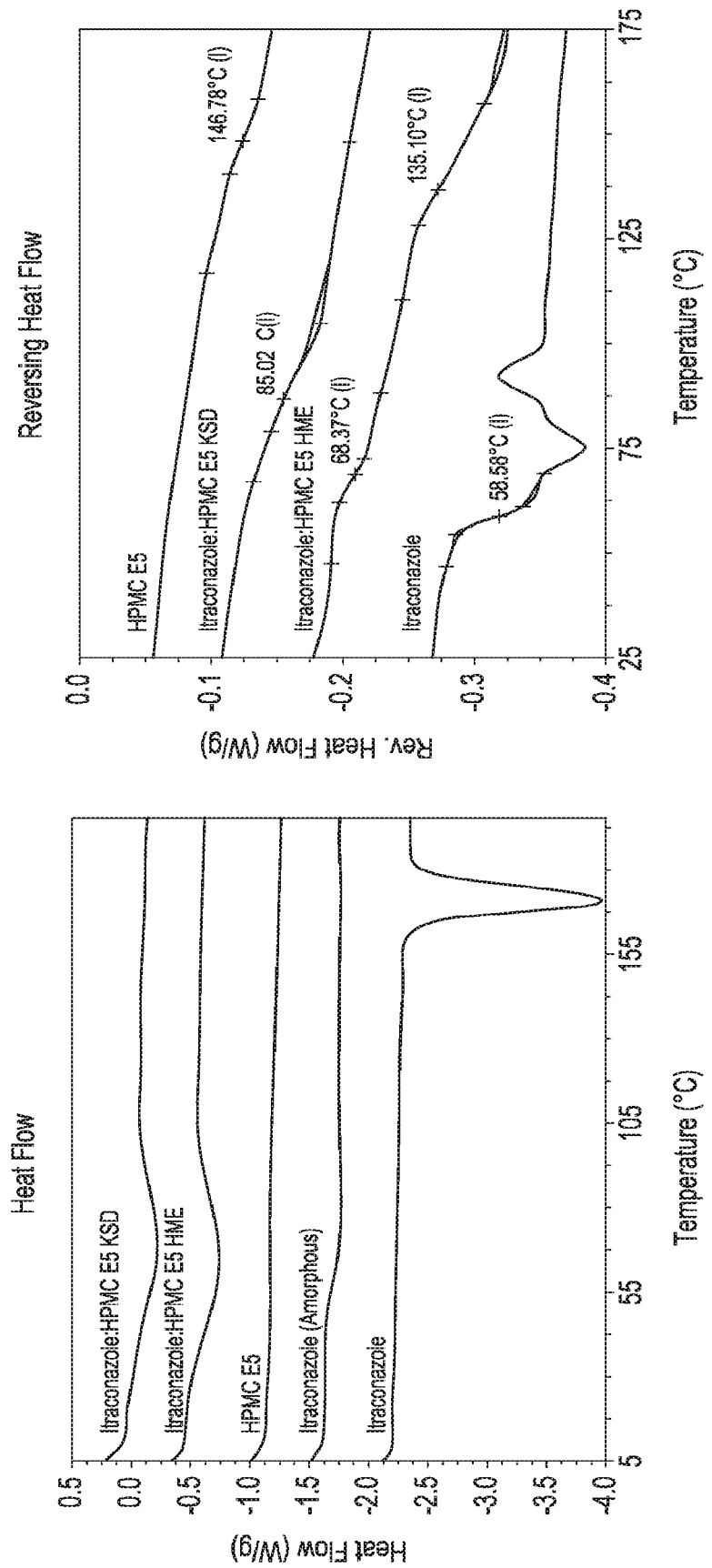
FIG. 13. DSC analysis of itraconazole:HPMC E5 processed by TKC and by HME.

Modulated Differential scanning calorimetry testing of itraconazole:HPMC E5 processed by TKC and by HME was performed using a TA Instruments Model 2920 DSC (New Castle, Del.) and analyzed using TA Universal Analysis 2000 Software. Samples were accurately weighed to 15±2 mg in aluminum crimped pans. Testing was performed at a ramp rate of 10° C./min from 5 to 215° C. using a modulation temperature amplitude of 0.5° C. and a modulation period of 40 s under nitrogen purge at a flow rate of 40 mL/min. Drug free compositions were heated a minimum of 50° C. above the glass transition temperature. The results are shown in FIG. 13.

Examination of the heat flow profile was use to evaluate the crystallinity of the compositions. Itraconazole exhibits a characteristic melting endotherm at 171° C., which was not present in the amorphous material. Additionally, this melting endotherm was absent in all processed compositions, supporting the amorphous nature observed by pXRD analysis. Reversing heat flow profiles were examined to determine the glass transition temperature of the compositions. ITZ:HPMC E5 compositions produced by HME and TKC both exhibited a glass transition temperature of approximately 115° C. tested, supporting an equivalent level of drug dispersion within the composition.

Itraconazole:L100-55 processed by TKC and HME were also tested. Supersaturated dissolution testing was performed based on the USP XXIX method A enteric dissolution test using a VK 7010 dissolution apparatus (Varian, Inc., Palo Alto, Calif.) and VK 8000 autosampler (Varian, Inc., Palo Alto, Calif.). An equivalent amount of 10×0.1N HCl media equilibrium solubility was weighed and added to the dissolution vessel containing 750 mL of 0.1N HCl media. After two hours, 250 mL of 0.2M $Na_3PO_4$ solution was added to the dissolution vessel to achieve a pH of approximately 6.8. During testing 5 mL samples were removed from the dissolution vessels without replacement after 120, 125, 130, 135, 150, 180 and 240 min. Samples were immediately filtered, diluted in a 1:1 ratio with mobile phase, vortexed mixed and transferred into 1 mL vials (VWR International, West Chester, Pa.) for analysis.

Figure 14:
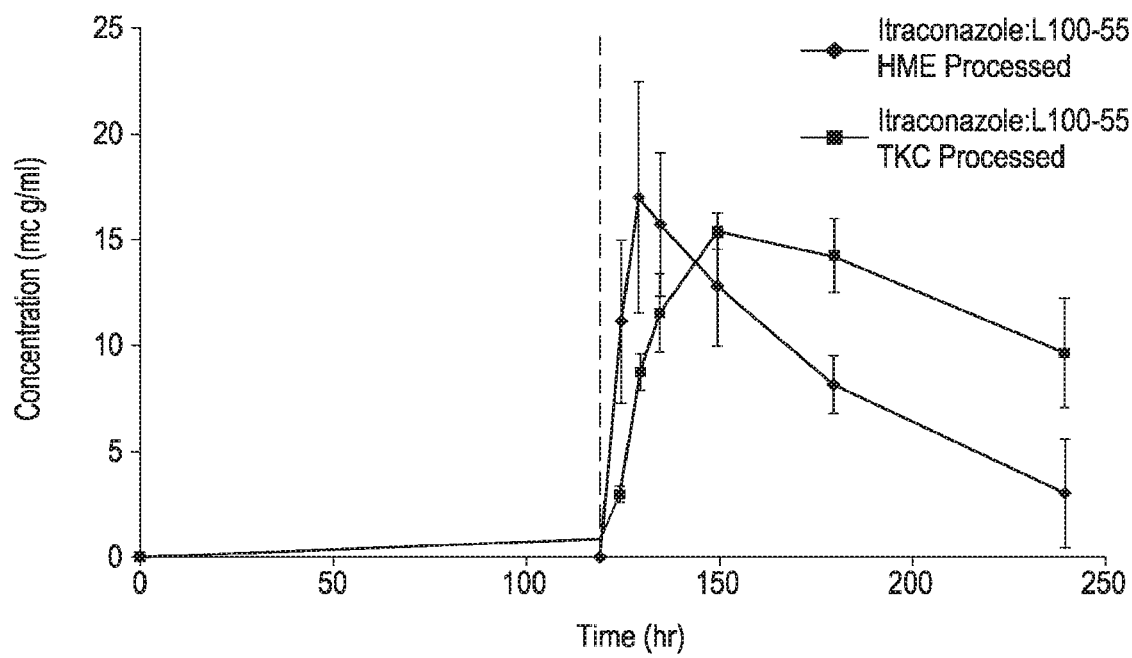
FIG. 14. Dissolution analysis of itraconazole:L100-55 processed by TKC and by HME.

Dissolution samples were analyzed using a Waters (Waters Corporation, Milford, Mass.) high performance liquid chromatography (HPLC) system consisting of dual Waters 515 Syringe Pumps, a Waters 717 Autosampler and a Waters 996 Photo Diode Array extracting at a wavelength of 263 nm. The system was operated under isocratic flow at 1 mL/min using a mobile phase consisting of 70:30:0.05 acetonitrile:water:diethanolamine equipped with a Phenomenex Luna 5 mcm C18(2) 100 Å, 150 mm×4.6 mm (Phenomenex®, Torrance, Calif.) HPLC column. Samples collected in the 0.1N HCl media and neutralized media were injected in volumes of 200 mL respectively during testing. Data were collected and analyzed using Empower® Version 5.0 software. The results of the itraconazole:L100-55 samples are shown in FIG. 14.

Itraconazole is a weakly basic drug, having a higher solubility in acidic media relative neutral media, it is still consider a poorly water soluble drug. Previous research has shown that pH change supersaturation test is the most representative in vitro test to assess compositional performance in vivo. Supersaturated dissolution testing is used to evaluate the dissolution rate and magnitude of supersaturation achieved by an amorphous composition. Testing results showed that both compositions exhibited similar overall dissolution profiles, with a longer tmax observed for TKC processed material. Although slightly slower release rates were observed from TKC processed materials, a longer duration of greater extent of supersaturation was also observed, indicating a potential for this composition to provide enhanced bioavailability. These performance differences may be due to the absence of plasticizer in TKC processed material.

Figure 15:
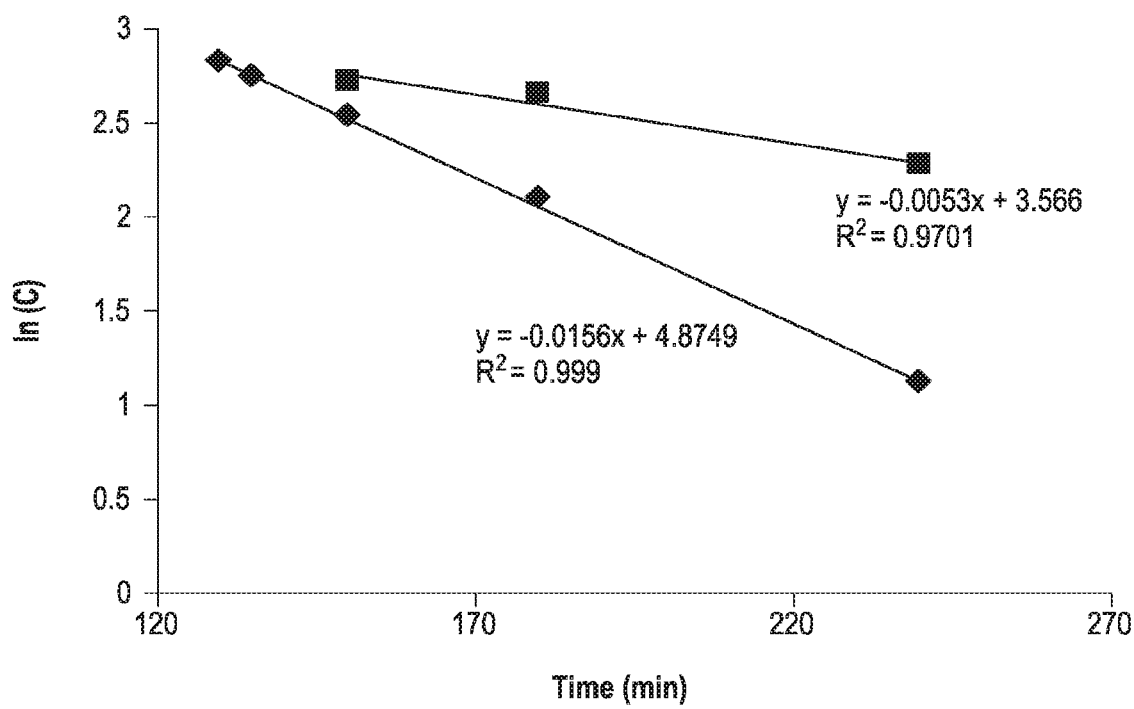
FIG. 15. Calculation of precipitation rates of itraconazole: L100-55 processed by TKC and HME.

Assessment of precipitation rates in vitro can be calculated by evaluation of the Supersaturated dissolution profile by identifying the maximum concentration achieved (Cmax) and performing a logarithmic transform on the data. The slope of the transformed data is correlated with the decay half life, with smaller calculated k values corresponding to longer supersaturated half life times. Results from the data analysis (FIG. 15) show that the composition produced by TKC yielded a longer supersaturated solution half life compared to HME produced compositions (131 min vs 44 min), which was attributed to the absence of plasticizer in the formulation. This performance could potentially result in higher bioavailabilities in vivo.

Figure 16:
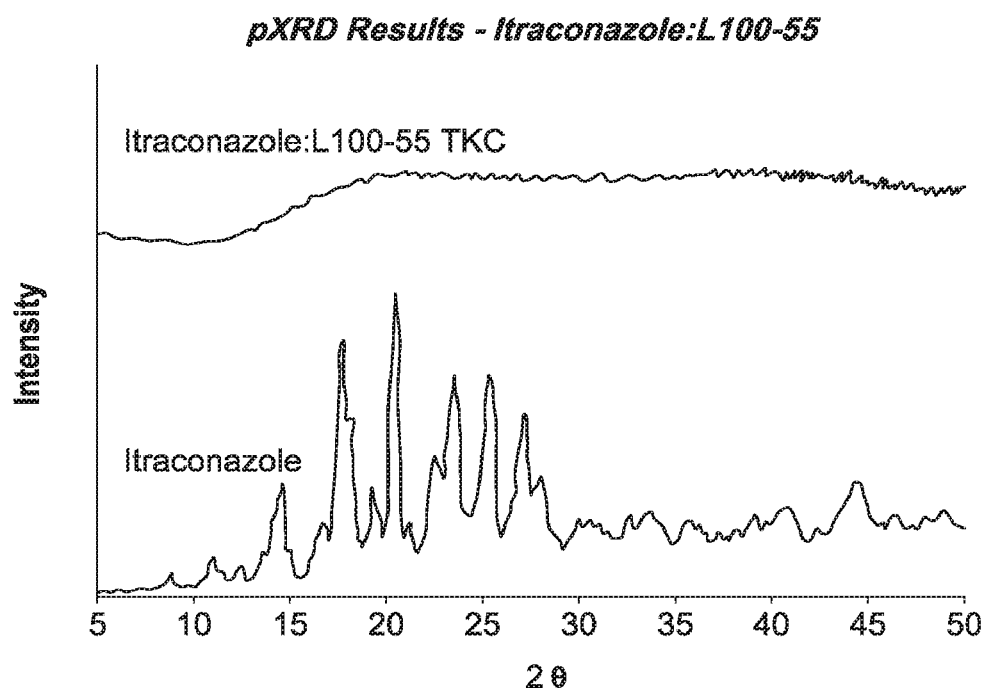
FIG. 16. XRD analysis of itraconazole:L100-55 processed by TKC.

XRD testing of itraconzaole:L100-55 processed by TKC was conducted using a Philips Model 1710 X-ray diffractometer (Philips Electronic Instruments Inc., Mahwah, N.J.). Samples of powder were placed into channeled stages and the diffraction profile was measured from 5° to 50° using a 2θ step size of 0.05° and dwell time of 3 s. The results are shown in FIG. 16.

XRD testing is used to evaluate the crystal structure of a material. Unprocessed itraconazole exhibits several characteristic peaks indicative of its crystallinity. These peak are absent in compositions of itraconazole and L100-55 processed by TKC indicating that material processed in both forms is amorphous.

Figure 17:
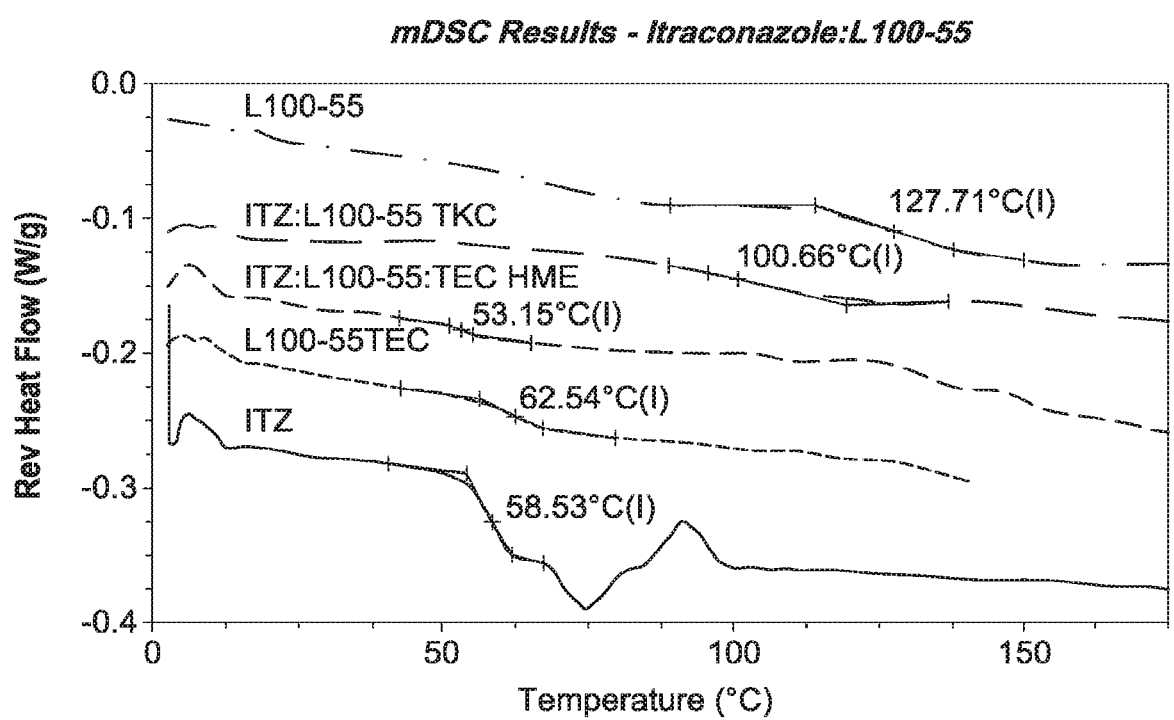
FIG. 17. DSC analysis of itraconazole:L100-55 processed by TKC and by HME with added plasticizer (TEC).

Modulated Differential scanning calorimetry testing for the itraconazole:L100-55 processed by TKC was performed and compared to itraconazole:L100-55 with added plasticizer (TEC) processed by HME. The tested were conducted on a TA Instruments Model 2920 DSC (New Castle, Del.) and analyzed using TA Universal Analysis 2000 Software. Samples were accurately weighed to 15±2 mg in aluminum crimped pans. Testing was performed at a ramp rate of 10° C./min from 5 to 215° C. using a modulation temperature amplitude of 0.5° C. and a modulation period of 40 s under nitrogen purge at a flow rate of 40 mL/min. Drug free compositions were heated a minimum of 50° C. above the glass transition temperature. The results are shown in FIG. 17.

Examination of reversing heat flow profiles can be used to assess the glass transition temperature of a composition. Results showed that the glass transition temperature of L100-55 was 127° C., corresponding well with previously published results. Plasticization at 20% w/w TEC reduces the temperature to 63° C. Compositions processed by HME containing TEC exhibited a glass transition temperature of 53° C. while compositions processed by TKC without the plasticizer exhibited glass transition temperatures of 101° C. This difference in glass transition temperature is extremely beneficial for providing enhanced long term stability of an amorphous composition.

This example demonstrates that solid dispersions of ITZ:L100-55 were successfully produced using TKC, with observed processing times under one minute and potencies within ±5% of target. XRD testing of TKC processed material exhibited an amorphous profile which was confirmed by the absence of crystalline drug melting endotherms in mDSC analysis. This, in combination with the single glass transition observed, indicated the amorphous solid solution nature of the composition. Glass transition temperatures ($T_g$) were identified using mDSC. Compositions produced without plasticizer using the TKC process exhibited Tg values of 100.7° C. while HME compositions containing TEC yielded Tg values of 53.2° C. Supersaturated dissolution testing showed no statistically significant difference between the maximum concentration achieved in vitro (TKC: 15.4±0.8 HME: 17.1±5.5 µg/ml), while compositions produced by TKC exhibited significantly reduced precipitation rates in neutral media.

In conclusion, compositions processed by TKC without the aid of a plasticizer exhibited higher Tg and reduced supersaturation precipitation rates in vitro, indicating that TKC processing can provide enhanced solid state properties and the potential for improved bioavailability of advanced solid dispersion formulations compared to those produced using traditional processing techniques.

Example 4

This study investigates the stability of a thermally unstable API in the TKC manufacturing process. Hydrocortisone is a drug that has been shown to exhibit degradation during thermal pharmaceutical processing. Since it was known that other thermal pharmaceutical processing techniques could generate hydrocortisone compositions, e.g., Repka et al. (44), the aim of this study was to test whether TKC processing could also generate compositions with a thermally unstable API. The amount of hydrocortisone degradation found in Repka et al. was shown to be proportional to the duration of processing with HME.

Pharmaceutical compositions of hydrocortisone were prepared by TKC, having an ejection temperature of approximately 160° C., and compared to the unprocessed drug substance to evaluate the formation of degradation products induced by processing. The hydrocortisone formulation processed by TKC is presented in Table 2.

TABLE 2

Formulation for Processing of Thermally Labile Compositions.

| Material | % w/w |
| --- | --- |
| Hydrocortisone, USP (Spectrum Chemical) | 10 |
| Kollidon VA 64 (BASF Corp.) | 90 |

Analytical testing of the hydrocortisone formulation processed by TKC was performed by HPLC using a Phenomenex C18 column and mobile phase of 65:35 methanol:water at a flow rate of 1 ml/min. Degradation products were identified and are described in terms of their retention time under this method. The results are presented in Table 3.

TABLE 3

Degradation Products for TKC Processed Materials.

| Description | Hydrocortisone, USP | TKC Processed Material |
| --- | --- | --- |
| Impurity - 3.2 | 0.20% | 0.20% |
| Impurity - 3.9 | 0.26% | 0.27% |
| Impurity - 4.9 | 0.20% | 0.20% |

TABLE 3-continued

Degradation Products for TKC Processed Materials.

| Description | Hydrocortisone, USP | TKC Processed Material |
| --- | --- | --- |
| Impurity - 5.5 | 0.62% | 0.64% |
| Deg. Product - 7.8 | ND | 0.05% |
| Impurity - 8.7 | 0.13% | 0.10% |

Analytical testing results indicated only minor degradation formation, which shows that TKC processing has surprisingly low API degradation during the process. For example, while there was no change in the levels of impurities, at 7.8 minutes only 0.05% degradation of hydrocortisone could be detected. This level of degradation is actually below the ICH Guidelines for reporting degradation products (45). Furthermore, mass balance testing showed that the TKC processed compositions exhibited 100.6% of theoretical potency, further revealing the ability of this process to minimize API degradation during processing. These results show that TKC significantly reduces degradation levels of APIs during processing, for example because of shorter processing times, as compared to HME. As shown in Ruka et al., HME resulted in significant degradation levels and product potencies that varied from approximately 70% to almost 94%. Thus, TKC results in lower degradation which means higher percentages of the API in composition products, and higher levels of product potency.

Example 5

This study focused on ternary solid dispersions with improved mixing. Multicomponent solid dispersions of itraconazole, Eudragit® L100-55 and Carbomer 974P produced by twin screw hot melt extrusion have been shown to exhibit two discrete phases attributed to the presence of a L100-55 dominated phase and a Carbomer dominated phase. Compositions of itraconazole, Eudragit® L100-55 and Carbomer 974P were processed by twin screw extrusion and TKC with the solid state attributes of the composites characterized by modulated differential scanning calorimetry (mDSC). Compositions of itraconazole:Eudragit® L100-55 were processed in a 1:2 ratio. Compositions containing Carbomer were produced using a Carbomer polymer level of 20%. For compositions processed by twin screw hot melt extrusion, 20% TEC was used as a plasticizer.

Figure 18:
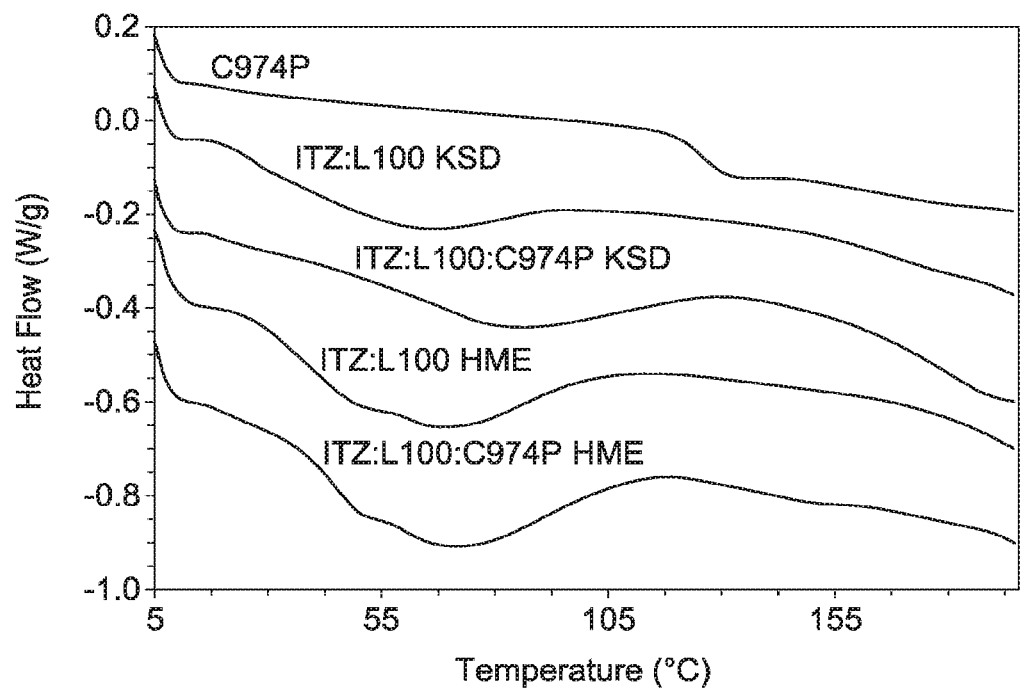
FIG. 18. mDSC heat flow profiles of Carbomer 974P, itraconazole:L100-55 composites, and itraconazole: Eudragit® L100-55:Carbomer 974P composites, processed by HME and TKC processed compositions.
Figure 19:
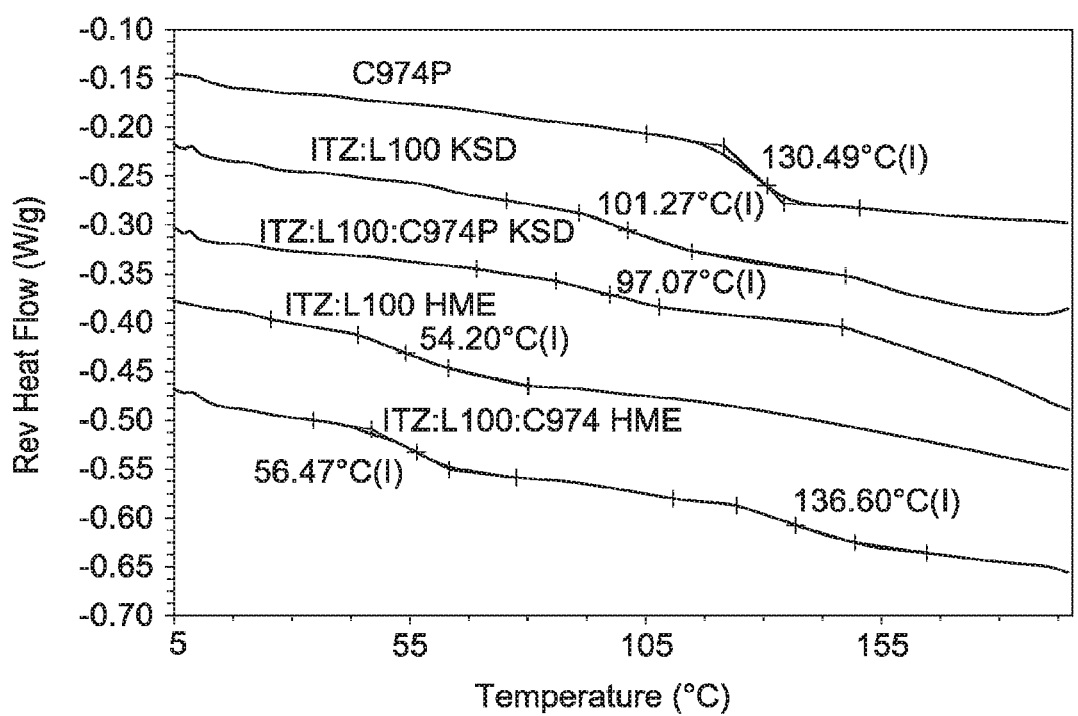
FIG. 19. mDSC reversing heat flow profiles are shown for the composites of FIG. 18.

Testing was conducted by weighing an approximately 15 mg sample and heating from 5 to 215° C. at a ramp rate of 10° C./min and amplitude of 0.5° C. Total heat flow profiles are presented in FIG. 18 for Carbomer 974P, itraconazole: L100-55 composites processed by TKC and HME, and itraconazole: Eudragit® L100-55:Carbomer 974P composites processed by TKC and HME. The results show a significant difference in the relaxation temperature onset of the itraconazole:Eudragit® L100-55:Carbomer 974P composite processed by TKC when compared to twin screw hot melt extrusion. Reversing heat flow profiles for these compositions are presented in FIG. 19. As shown in FIG. 19, Itraconazole:Eudragit® L100-55:Carbomer 974P formulations processed by TKC exhibited a single phase while compositions produced by twin screw hot melt extrusion exhibited two discrete phases which corresponded to a Eudragit® L100-55 dominated phase and a Carbomer 974P dominated phase.

This study shows that TKC achieves more intimate mixing of API with pharmaceutically acceptable excipient(s), as compared to HME. Thus, when HME generates a composition with two or more glass transition temperatures, TKC may be able to generate a composition with a single glass transition temperature using the same combination of APIs and excipients. TKC may also be able to adjust the release properties and stability of a composition comprising various APIs and excipients, including known composition mixtures. Such a TKC processed composition will have a higher single glass transition temperature than the lower of the two or more glass transition temperatures of the first composition. This will result in a more stable composition, likely with a longer shelf life. Thus, pharmaceutical compositions with poor shelf-life may be amenable to processing by TKC, resulting in improved stability and shelf-life.

Example 6

Figure 20:
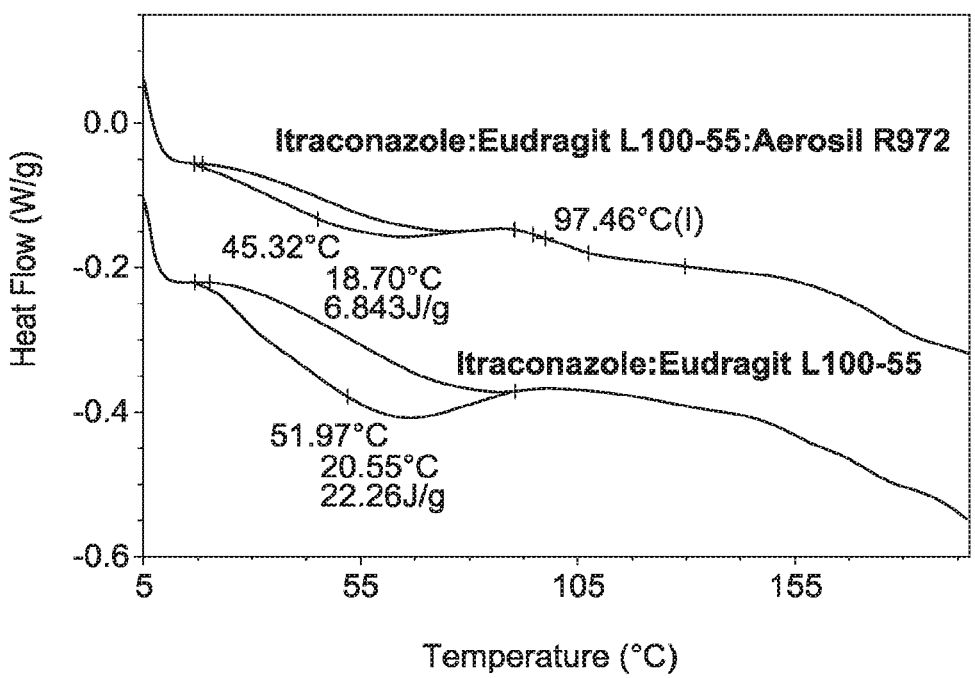
FIG. 20. Heat flow profile of TKC processed composites containing Aerosil R972 compared to Aerosil R972-free composites.
Figure 21:
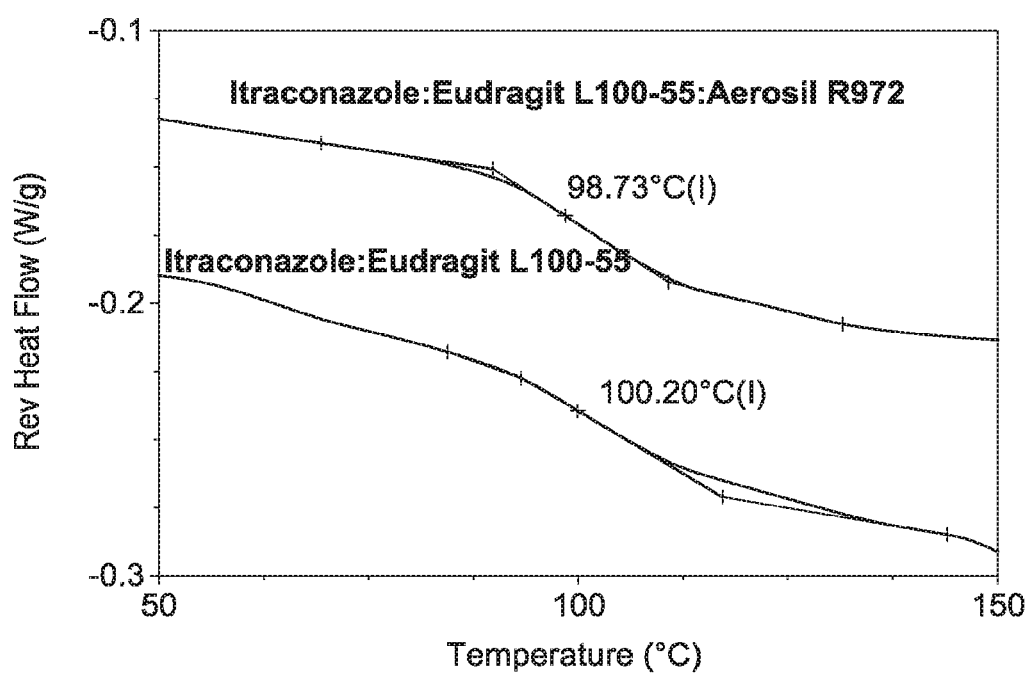
FIG. 21. Reversing heat flow profiles are shown for the composites of FIG. 20.

This Example is directed to the use of functional additives for nanoconfinement. Polymer matrix-based nanocomposites offer the ability to modify properties of pharmaceutical composition, e.g., to effect the relaxation of materials, glass transition temperatures, stability, drug release rates, moisture uptake, and the like. To study this potential application, Aerosil R972, a hydrophobic fumed silica, was incorporated into a pharmaceutical composition of itraconazole and Eudragit® L100-55 prepared by TKC and compared to a composition without the fumed silica. These compositions were evaluated by mDSC to assess changes in glass transition. Testing was conducted by weighing an approximately 15 mg sample and heating from 5 to 215° C. at a ramp rate of 10° C./min and amplitude of 0.5° C. Total heat flow profiles, presented in FIG. 20, show that the composition containing Aerosil R972 exhibited a weaker relaxation event compared to the Aerosil 8972 free composition. The composition containing Aerosil R972 also had a visible glass transition event. Reversing heat flow profiles, presented in FIG. 21, clearly show a slight decrease in temperature for the glass transition event. These results are in line with results described in a review article by Paul and Robeson (46), discussing changes in physical properties due to confinement effects.

The present disclosure thus establishes TKC as a novel and improved technology for producing pharmaceutical solid dispersion systems. As a solvent-free, efficient, scaleable manufacturing process, TKC possesses many of the attributes which made HME a preferred pharmaceutical manufacturing process. With regard to producing amorphous solid dispersion systems in thermally stable polymeric carriers, this disclosure demonstrates the dose similarity between the two processes. However, the unique attributes of TKC, i.e., very brief processing times, reduced processing temperatures, and no-flow molten processing, distinguish TKC as a superior technology to HME, particularly in regards to processing of thermolabile materials as well as high $T_g/T_m$/melt viscosity materials. By successfully producing amorphous compositions of high melting point drugs in a thermolabile polymer without the use of processing aids, this disclosure demonstrates TKC to be a considerable advancement in solid dispersion manufacturing technology. Although the disclosures is focused on the use of TKC for the production of amorphous solid dispersion systems, it is believed that TKC, TKM, and all variations in between have numerous and diverse applications to pharmaceutical manufacturing.

It is contemplated that any embodiment discussed in this specification can be implemented with respect to any API, excipient, carrier method, kit, reagent, or composition of the present invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Lipinski, C. A. Avoiding investment in doomed drugs, is poor solubility an industry wide problem? Current Drug Discovery 2001:17-9.
2. Lipinski, C. A., Lombardo, F., Dominy, B. W., Feeney, P. J. Experimental and computational approaches to estimate solubility and permeability in drug discovery and development settings. Advanced Drug Delivery Reviews 1997; 23(1-3):3-25.
3. Lipinski, C. A. Poor Aqueous Solubility—an Industry Wide Problem in Drug Delivery. American Pharmaceutical Review 2002; 5:82-5.
4. Serajuddin, A. T. M. Solid Disperison of Poorly Water-Soluble Drugs: Early Promises, Subsequent Problems, and Recent Breakthroughs. Journal of Pharmaceutical Sciences 1999; 88(10):1058-66.
5. Noyes, A. A., Whitney, W. R. The rate of dissolution of solid substances in their own solutions. Journal of the American Chemical Society 1897; 19:930-4.
6. Sinswat, P., Gao, X., Yacaman, M. J., Williams Iii, R. O., Johnston, K. P. Stabilizer choice for rapid dissolving high potency itraconazole particles formed by evaporative precipitation into aqueous solution. International Journal of Pharmaceutics 2005; 302(1-2):113-24.
7. Brittain, H. G., Grant, D. J. W. Effects of Polymorphism and Solid-State Solvation on Solubility and Dissolution Rate. In: Brittain, H. G., ed. Polymorphism in Pharmaceutical Solids. Boca Raton, Fla.: Informa Health Care; 1999:279-330.
8. Chowdary, K. P. R., Babu, K. V. V. S. Dissolution, bioavailability and ulcerogenic studies on solid dispersions of indomethacin in water-soluble cellulose polymers. Drug Development and Industrial Pharmacy 1994; 20(5):799-813.
9. Chen, X., Young, T. J., Sarkari, M., Williams, I., Robert O., Johnston, K. P. Preparation of cyclosporine A nanoparticles by evaporative precipitation into aqueous solution. International Journal of Pharmaceutics 2002; 242(1-2):3-14.
10. Sekikawa, H., Arita, T., Nakano, M. Dissolution behaviors and gastrointestinal absorption of phenytoin in phenytoin-polyvinylpyrrolidine coprecipitate. Chemical and Pharmaceutical Bulletin 1978; 26:118-26.
11. Jung, J,-Y., Yoo, S. D., Lee, S.-H., Kim, K.-H., Yoon, D.-S., Lee, K,-H. Enhanced solubility and dissolution rate of itraconazole by a solid dispersion technique, International Journal of Pharmaceutics 1999; 187(2):209-18.
12. Rogers, T. L., Johnston, K, P., Williams III, R. O. Solution-Based Particle Formation of Pharmaceutical Powders by Supercritical or Compressed Fluid Co2 and Cryogenic Spray-Freezing Technologies. Drug Development and Industrial Pharmacy 2001; 27(10):1003-15.
13. Hu, J., Johnston, K. P., Williams III, R. O. Nanoparticle Engineering Processes for Enhancing the Dissolution Rates of Poorly Water Soluble Drugs. Drug Development and Industrial Pharmacy 2004; 30(3):233-45.
14. Leuner, C., Dressman, J. Improving drug solubility for oral delivery using solid dispersions. European journal of Pharmaceutics and Biopharmaceutics 2000; 50(1):47-60.
15. Breitenbach, J. Melt extrusion: from process to drug delivery technology. European Journal of Pharmaceutics and Biopharmaceutics 2002; 54(2):107-17.
16. Goldberg, A. H., Gibaldi, M., Kanig, J. L. Increasing dissolution rates and gastrointestinal absorption of drugs via solid solutions and eutectic mixtures II. Experimental evaluation of eutectic mixture: urea-acetaminophen system. Journal of Pharmaceutical Sciences 1966; 55:48$^2$-7.
17. Goldberg, A. H., Gibaldi, M., Kanig, J. L., Mayersohn, M. Increasing dissolution rates and gastrointestinal absorption of drugs via solid dispersion in eutectic mixtures IV. Chloramphenicol-urea system. Journal of Pharmaceutical Sciences 1966; 55:581-3.
18. Chiou, W. L., Riegelman, S. Preparation and dissolution characteristics of several fast-release solid dispersions of griseofulvin. Journal of Pharmaceutical Sciences 1969; 58:1505-9.
19. Summers, M. P., Enever, R. P. Preparation and properties of solid dispersion system containing citric acid and primidone. Journal of Pharmaceutical Sciences 1976; 65:1613-161.
20. Goldberg, A. H., Gibaldi, M., Kanig, J. L. Increasing dissolution rates and gastrointestinal absorption of drugs via solid solutions and eutectic mixtures I. Theoretical considerations and discussion of the literature. Journal of Pharmaceutical Sciences 1965; 54:1145-8.
21. Repka, M., Koleng, J., Zhang, F., McGinity, J. W. Hot-Melt Extrusion Technology. In: Swarbrick, J., Boylan, J., eds. Encyclopedia of Phamaceutical Technology. 2nd ed. New York: Marcel Dekker, Inc; 2002.
22. Aitken-Nichol, C., Zhang, F., McGinity, J. W. Hot Melt Extrusion of Acrylic Films. Pharmaceutical Research 1996; 13(5):804-8.
23. Zhang, F., McGinity, J. W. Properties of Sustained-Release Tablets Prepared by Hot-Melt Extrusion. Pharmaceutical Development and Technology 1999; 4(2):241-50.
24. Zhang, F., McGinity, J. W. Properties of Hot-Melt Extruded Theophylline Tablets Containing Poly(Vinyl Acetate). Drug Development and Industrial Pharmacy 2000; 26(9):931-42.
25. Repka, M. A., McGinity, J. W. Hot-melt extruded films for transmucosal & transdermal durg delivery applications. Drug Delivery Technology 2004; 4(7):40, 2, 4-7.
26. Rambali, B., Verreck, G., Baert, L., Massart, D. L. Itraconazole Formulation Studies of the Melt-Extrusion Process with Mixture Design. Drug Development and Industrial Pharmacy 2003; 29(6):641-52.
27. Hulsmann, S., Backensfeld, T., Keitel, S., Bodmeier, R. Melt extrusion—an alternative method for enhancing the dissolution rate of 17[beta]-estradiol hemihydrate. European Journal of Pharmaceutics and Biopharmaceutics 2000; 49(3):237-42.
28. de Brabander, C., Vervaet, C., Remon, J. P. Development and evaluation of sustained release mini-matrices prepared via hot melt extrusion. Journal of Controlled Release 2003; 89(2):235-47.
29. Crowley, M. M., Fredersdorf, A., Schroeder, B., Kucera, S., Prodduturi, S., Repka, M. A., McGinity, J. W. The influence of guaifenesin and ketoprofen on the properties of hot-melt extruded polyethylene oxide films. European Journal of Pharmaceutical Sciences 2004; 22(5):409-18.
30. Six, K., Leuner, C., Dressman, J., Verreck, G., Peeters, J., Blaton, N., Augustijns, P., Kinget, R., Van den Mooter, G. Thermal Properties of Hot-Stage Extrudates of itraconazole and Eudragit E100. Phase separation and polymorphism. Journal of Thermal Analysis and calorimetry 2002; 68(2):591-601.
31. Six, K., Verreck, G., Peeters, J., Brewster, M. E., Van den Mooter, G. Increased physical stability and improved dissolution properties of itraconazole, a class II drug, by solid dispersions that combine fast- and slow-dissolving polymers. Journal of Pharmaceutical Sciences 2004; 93(1):124-31.
32. Verreck, G., Six, K., Van den Mooter, G., Baert, L., Peeters, J., Brewster, M. E. Characterization of solid dispersions of itraconazole and hydroxypropylmethylcellulose prepared by melt extrusion—part I. international Journal of Pharmaceutics 2003; 251(1-2):165-74.
33. Forster, A., Hempenstall, J., Tucker, I., Rades, T. Selection of excipients for melt extrusion with two poorly water-soluble drugs by solubility parameter calculation and thermal analysis. International Journal of Pharmaceutics 2001; 226(1-2):147-61.
34. Breitenbach, J. Melt extrusion can bring new benefits to HIV therapy: the example of Kaletra tablets. American Journal of Drug Delivery 2006; 4(2):61-4.
35. Top 200 Drugs for 2006 by Sales. Drugs.com, 2007. (Accessed Aug. 6, 2007, 2007, at www.drugs.com/top200.html.)
36. Dittgen, M., Fricke, S., Gerecke, H., Osterwald, H. Hot spin mixing—a new technology to manufacture solid dispersions. Part 1: Testosterone. Pharmazie 1995; 50(3): 225-6.
37. Hamaura, T., Newton, M. N. Interaction between Water and Polyvinylpyrrolidone) Containing Polyethylene Glycol. Journal of Pharmaceutical Sciences 1999; 88(11): 1228-33.
38. Park, B. D., Balatinecz, J. J. A comparison of compounding processes for wood-fiber/thermoplastic composites. Polymer Composites 1997; 18(3):425-31.
39. Gopakumar, T., Pagé, D. J. Y. S. Compounding of nanocomposites by thermokinetic mixing. Journal of Applied Polymer Science 2005; 96(5):1557-63.
40. Gopakumar, T., Pagé, D. J. Y. S. Polypropylene/graphite nanocomposites by thereto-kinetic mixing. Polymer Engineering and Science 2004; 44(6):1162-9.
41. Six, K., Berghmans, H., Leuner, C., Dressman, J., Van Werde, K., Mullens, J., Benoist, L., Thimon, M., Meublat, L., Verreck, G., Peeters, J., Brewster, M., Van den Mooter, G. Characterization of Solid Dispersions of Itraconazole and Hydroxypropylmethylcellutose Prepared by Melt Extrusion, Part II. Pharmaceutical Research 2003; 20(7): 1047-54.
42. Glomme, A., März, J., Dressman, J. Comparison of a miniaturized shake-flask solubility method with automated potentiometric acid/base titrations and calculated solubilities. Journal of Pharmaceutical Sciences 2005; 94(1):1-16.
43. Petereit, H.-U., Weisbrod, W. Formulation and process considerations affecting the stability of solid dosage forms formulated with methacrylate copolymers, European Journal of Pharmaceutics and Biopharmaceutics 1999; 47(1):15-25.
44. Repka, A., Gerding, T., Repka, S., McGinity, J. Influence of plasticizers and drugs on the physical-mechanical properties of hydroxypropylcellulose films prepared by hot melt extrusion. Drug Development and Industrial Pharmacy 1999; 25(5):625-33.
45. ICH Harmonised Tripartite Guideline, impurities in New Drug Products Q3B(R2); Current Step 4 version, dated Jun. 2, 2006.
46. Paul, D. R., Robeson, L. M. Polymer nanotechnology: Nanocomposites. Polymer 2008; 49:3187-3204.

What is claimed is:

1. A pharmaceutical composition comprising at least one active pharmaceutical ingredient (API) with at least one pharmaceutically acceptable excipient thermokinetically processed into a composite, wherein the at least one API comprises a thermally labile or poorly water-soluble API, and wherein the composite is processed at an average temperature that is at or below a glass transition temperature or a melting point of the at least one API.

2. The pharmaceutical composition of claim 1, wherein the at least one pharmaceutically acceptable excipient comprises a polymer having a high melt viscosity.

3. The pharmaceutical composition of claim 1, wherein the at least one pharmaceutically acceptable excipient comprises a polymer selected from the group consisting of methylcellulose, ethylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, hydroxypropyl methylcellulose acetate succinate, cellulose acetate phthalate, cellulose acetate trimellate, hydroxypropyl methylcellulose phthalate, cellulose acetate butyrate, polyvinylpyrrolidones, polyacrylates, polymethacrylates, polyvinyl alcohols, polyethylene glycols, polyvinyl acetate polyvinylpyrrolidone copolymers, polyethylene oxides, dimethylaminoethyl methacrylate-methacrylic acid ester copolymers, ethylacrylate-methylmethacrylate copolymers, poly(methyacrylate ethylacrylate) copolymers, poly(methacrylate methylmethacrylate) copolymers, starches, pectins, polysaccharides, gum arabic, guar gum, and xanthan gum.

4. The pharmaceutical composition of claim 1, wherein the composition comprises less than about 1.0% degradation products of the at least one API.

5. The pharmaceutical composition of claim 1, wherein, after processing, the at least one API has at least about 94% drug potency as compared to the at least one API before processing.

6. The pharmaceutical composition of claim 1, wherein the pharmaceutical composition does not comprise a processing agent.

7. The pharmaceutical composition of claim 1, wherein the composite is a single phase, amorphous composite.

8. The pharmaceutical composition of claim 1, wherein the at least one API comprises a molecule selected from the group consisting of a small organic molecule, a protein, a peptide, and a polynucleic acid.

9. The pharmaceutical composition of claim 1, wherein the composite is further processed by hot melt extrusion, melt granulation, compression molding, tablet compression, capsule filling, film-coating, or injection molding.

10. The pharmaceutical composition of claim 1, wherein the composite is shaped into a dosage form that is a tablet, a capsule, or a pellet.

* * * * *